US012714767B2

(12) United States Patent
Magin et al.

(10) Patent No.: US 12,714,767 B2
(45) Date of Patent: Aug. 25, 2026

(54) HYBRID-HYDROGELS COMPRISING DECELLULARIZED EXTRACELLULAR MATRIX

(71) Applicant: The Regents of the University of Colorado, A Body Corporate, Denver, CO (US)

(72) Inventors: Chelsea Magin, Denver, CO (US); Cassandra Petrou, Denver, CO (US); Rukshika Shalani Hewawasam, Denver, CO (US)

(73) Assignee: THE REGENTS OF THE UNIVERSITY OF COLORADO, A BODY CORPORATE, Denver, CO (US)

(*) Notice: Subject to any disclaimer, the term of this patent is extended or adjusted under 35 U.S.C. 154(b) by 627 days.

(21) Appl. No.: 17/915,201

(22) PCT Filed: Apr. 2, 2021

(86) PCT No.: PCT/US2021/025539
§ 371 (c)(1),
(2) Date: Sep. 28, 2022

(87) PCT Pub. No.: WO2021/202974
PCT Pub. Date: Oct. 7, 2021

(65) Prior Publication Data

US 2023/0135999 A1 May 4, 2023

Related U.S. Application Data

(60) Provisional application No. 63/004,888, filed on Apr. 3, 2020.

(51) Int. Cl.

| | |
|---|---|
| ***A61L 27/52*** | (2006.01) |
| ***A61L 27/14*** | (2006.01) |
| ***A61L 27/36*** | (2006.01) |
| ***A61L 27/38*** | (2006.01) |

(52) U.S. Cl.
CPC ............... *A61L 27/52* (2013.01); *A61L 27/14* (2013.01); *A61L 27/3633* (2013.01); *A61L 27/3804* (2013.01)

(58) Field of Classification Search
CPC ...... A61L 27/52; A61L 27/14; A61L 27/3633; A61L 27/3804; A61L 27/16; A61L 27/50; A61L 27/58; C12N 2533/90; C12N 2537/10; C12N 5/0068
See application file for complete search history.

(56) References Cited

U.S. PATENT DOCUMENTS

| | | | | |
|---|---|---|---|---|
| 2010/0152414 A1 | | 6/2010 | Zhao et al. | |
| 2011/0177590 A1 | | 7/2011 | Clyne et al. | |
| 2012/0100185 A1* | | 4/2012 | Wen ........................ | A61P 43/00 977/773 |
| 2012/0202263 A1 | | 8/2012 | Blakely et al. | |
| 2016/0202241 A1 | | 7/2016 | Floren et al. | |
| 2016/0375174 A1 | | 12/2016 | Seliktar et al. | |
| 2017/0239289 A1 | | 8/2017 | Av-Gay et al. | |
| 2018/0246411 A1 | | 8/2018 | Zustiak et al. | |
| 2019/0345227 A1 | | 11/2019 | Sun et al. | |
| 2020/0347359 A1 | | 11/2020 | Magin et al. | |

FOREIGN PATENT DOCUMENTS

WO 2019136453 A1 7/2019

OTHER PUBLICATIONS

Cao et. al. "3-D cell encapsulation in gelatin and elastin poly (ethylene glycol)hybrid hydrogel for elastic tissue remolding" Front. Bioeng. Biotechnol. Conference Abstract: 10th World Biomaterials Congress. 2016. (Year: 2016).*

Grover et. al. "Myocardial matrix-polyethylene glycol hybrid hydrogels for tissue engineering" Nanotechnology 25 (2014) 014011, 1-12. (Year: 2014).*

Petrou et. al. "Clickable, hybrid hydrogels as tissue culture platforms for modeling chronic pulmonary diseases in vitro." Reserach Portal—Society for Biomaterials Annual Meeting and Exposition 2019. 2019 (Year: 2019).*

Dunphy et. al. "Hydrogels forlungtissueengineering:Biomechanical properties ofthincollagen-elastin constructs" Journal of the Mechanical Behavior of Biomedical Materials, 38, (2014) 251-259. (Year: 2014).*

Grover et. al. "Myocardial matrix-polyethylene glycol hybrid hydrogels for tissue engineering" Nanotechnology 25 (2014) 014011 (12pp). (Year: 2014).*

Cao et. al "3-D cell encapsulation in gelatin and elastin poly (ethylene glycol)hybrid hydrogel for elastic tissue remolding" Front. Bioeng. Biotechnol. Conference Abstract: 10th World Biomaterials Congress. 2016. doi: 10.3389/conf.FBIOE.2016.01.01992 (Year: 2016).*

Tong et. al. "A New End Group Structure of Poly(ethylene glycol) for Hydrolysis-Resistant Biomaterials" Journal of Polymer Science: Part A: Polymer Chemistry. p. 1513-1516. (Year: 2011).*

Lewis et. al. "In vitro model alveoli from photodegradable microsphere templates" Biomater. Sci., 2015, 3, 821. (Year: 2015).*

Stowers, et al. "Dynamic phototuning of 3D hydrogel stiffness" PNAS | Feb. 17, 2015 | vol. 112 | No. 7 | 1953-8. (Year: 2015).*

Kim "Characterization of the crosslinking kinetics of multi-arm poly(ethylene glycol) hydrogels formed via Michael-type addition" Soft Matter. Feb. 21, 2016; 12(7): 2076-2085. (Year: 2016).*

Li "Evaluation of the bioactivity about anti-sca-1/basic fibroblast growth factor-urinary bladder matrix scaffold for pelvic reconstruction" Journal of Biomaterials Applications 2019 v33, 808-818. (Year: 2019).*

(Continued)

*Primary Examiner* — Ali Soroush
*Assistant Examiner* — Rajan Pragani
(74) *Attorney, Agent, or Firm* — CANTOR COLBURN LLP

(57) ABSTRACT

The present invention relates in part to hybrid hydrogel scaffolds including a decellularized extracellular matrix (dECM) tissue, and a synthetic polymer. The dECM may include any suitable tissue including for example, lung tissue, heart tissue, heart-lung block tissue, skin tissue, liver tissue, pancreatic tissue, kidney tissue, and the like.

20 Claims, 20 Drawing Sheets

(56) References Cited

OTHER PUBLICATIONS

Cao "Synthesis of stiffness-tunable and cell-responsive gelatin-poly(ethylene glycol) hydrogel for three-dimensional cell encapsulation" Journal of Biomedical Materials Research A | Oct. 2016 vol. 104A, Issue 10 (Year: 2016).*
Prof Steven Abbott "Modulus Conversions" (2026) https://www.stevenabbott.co.uk/practical-mechanical/Modulus-Conversions.php (Year: 2026).*
Cao "Synthesis of stiffness-tunable and cell-responsive gelatin-poly(ethylene glycol) hydrogel for three-dimensional cell encapsulation" Journal of Biomedical Materials Research A, 2016. (Year: 2016).*
Grover "Myocardial matrix-polyethylene glycol hybrid hydrogels for tissue engineering" Nanotechnology, 2014. (Year: 2014).*
Dunphy "Hydrogels for lung tissue engineering: Biomechanical properties of thin collagen-elastin constructs" Journal of the Mechanical Behavior of Biomedical Materials, 2014. (Year: 2014).*
Tong "A New End Group Structure of Poly(ethylene glycol) for Hydrolysis-Resistant Biomaterials" Journal of Polymer Science: Part A: Polymer Chemistry, 2011. (Year: 2011).*
Stowers "Dynamic phototuning of 3D hydrogel stiffness" (PNAS, 2015) (Year: 2015).*
Lewis "In vitro model alveoli from photodegradable microsphere templates" (Biomater. Sci., 2015) (Year: 2015).*
Visser "Crosslinkable Hydrogels Derived from Cartilage, Meniscus, and Tendon Tissue" Tissue Engineering Part A, 2015. (Year: 2015).*
Li "Evaluation of the bioactivity about anti-sca-1/basic fibroblast growth factor-urinary bladder matrix scaffold for pelvic reconstruction" Journal of Biomaterials Applications, 2018. (Year: 2018).*
Extended European Search Report issued in Application No. 19735804.7 on Sep. 6, 2021, 8 pages.
International Search Report for International Application No. PCT/US2019/12722 filed on Jan. 8, 2019, Date of Mailing: May 23, 2019, 6 pages.
International Search Report issued in Application No. PCT/US2021/025539 on Jul. 22, 2021, 3 pages.
Katherine J.R. Lewis et al., "In vitro model alveoli from photodegradable microsphere templates", Biomaterials Science, Royal Society of Chemistry, vol. 3, 2015, pp. 821-832.
Petrou, CL et al., "Clickable, hybrid hydrogels as tissue culture platforms for modeling chronic pulmonary diseases in vitro", Transactions of the Annual Meeting of the Society for Biomaterials and the Annual International Biomaterials Symposium, vol. 40, Apr. 3-6, 2019.
Written Opinion for International Application No. PCT/US2019/12722 filed on Jan. 8, 2019, Date of Mailing: May 23, 2019, 9 pages.
Written Opinion issued in Application No. PCT/US2021/025539 on Jul. 22, 2021, 6 pages.
Xinming Tong et al., "A New End Group Structure of Poly(ethylene glycol) for Hydrolysis-Resistant Biomaterials", Journal of Polymer Science: Part A: Polymer Chemistry, vol. 49, pp. 1513-1516, Jan. 2011.
Zhang et al. "The reconstructions of lung alveolus-like structure in collagen-matrigel/microcapsules scaffolds in vitro" J. Cell. Mol. Med., 2011, vol. 15, No. 9, pp. 1878-1886, abstract p. 1884.
Petrou et al. "Clickable decellularized extracellular matrix as a new tool for building hybrid-hydrogels to model chronic fibrotic diseases in vitro" J. Mater. Chem. B, Apr. 17, 2020, 8, 6814-6826.
Wilkinson et al., "Development of a Three-Dimensional Bioengineering Technology to Generate Lung Tissue for Personalized Disease Modeling", Stem Cells Translational Medicine, vol. 6, 2017; 13 pages.
Souza et al., "Three-dimensional tissue culture based on magnetic cell levitation," Nature Nanotechnology, 2010, pp. 291-296, vol. 5.
Ahmadi et al., "Chitosan based hydogels: characteristics and pharmaceutical applications", Research in Pharmaceutical Science, 2015; 10(1): 1-16.
Caracena_Blomberg_2022_3D Lung Models Biomater. Sci., 2022, 10, 7133-7148 and Supplemental Material.
Fairbanks et al. Biomaterials 30 (2009) 6702-6707.
Kloxin et al., Synthesis of Photodegradable hydrogels as dynamically turnable cell culture platforms, Nat. Protoc. 2010, 5, 1867-1887.
Kolhatkar et al., Magnetic Sensing Potential of Fe3O4 Nanocubes Exceeds That of Fe3O4 Nanospheres, ACS Omega, 2017, 2, 8010-8019.
Nair et al., "Enhanced two-stage reactive polymer network forming systems", Polymer, 2012; 53:2429-2434.
Sugaya et al., "Manipuliation of cells and cell spheroids using collagen hydrogel microbeads prepared by microfluidic devices" 2012, International Symposium on Micro-NanoMechatronics and Human Science (MHS), Nogoya Japan, 2012 pp. 435-438, doi: 10.1109/MHS.2012.6492486.
Tan et al, "Novel Multi-arm PEG-based Hydrogels for Tissue Engineering", J Biomed Mater Res A 2010; 92(3): 979-987.
Calle et al. Acta Biomater. Author manuscript available in PMC Dec. 1, 2017. PMCID: PMC5451113 NIHMSID: NIHMS829039 PMID: 27693690.
Hoffman et al. Regional and Disease Specific Human Lung Extracellular Matrix Composition Open Manuscript (2022).

* cited by examiner

Soft

Stiffened

HYBRID-HYDROGELS COMPRISING DECELLULARIZED EXTRACELLULAR MATRIX

CROSS REFERENCE TO RELATED APPLICATIONS

This application is a National Stage application of PCT/US2021/025539, filed Apr. 2, 2021, which claims priority to U.S. Provisional Patent Application No. 63/004,888, filed Apr. 3, 2020, each of which is incorporated herein by reference in its entirety for all purposes.

STATEMENT REGARDING FEDERALLY SPONSORED RESEARCH OR DEVELOPMENT

This invention was made with government support under 1941401 awarded by the National Science Foundation. The government has certain rights in the invention.

BACKGROUND OF THE INVENTION

Hydrogels made only of decellularized extracellular matrix (dECM) do not have robust mechanical properties and are therefore hard to use as model systems. Fully synthetic hydrogels do not contain the complex biochemical cues that exist within dECM. Novel hydrogels that allow for more relevant models of disease and regeneration are needed in the art. The present invention addresses this need.

SUMMARY

In an embodiment, a hybrid hydrogel scaffold comprises a decellularized extracellular matrix (dECM) tissue, and a synthetic polymer crosslinked to the dECM, wherein the dECM is thiolated and wherein the synthetic polymer has a photo-tunable stiffness.

In another embodiment, a hybrid hydrogel system comprises a decellularized extracellular matrix (dECM), a synthetic polymer, chemically crosslinked with the dECM, and a plurality of cells, wherein the synthetic polymer has a photo-tunable stiffness.

In yet another embodiment, a method for generating a hybrid hydrogel comprises preparing a thiolated dECM, preparing a synthetic polymer solution, chemically crosslinking the dECM and the synthetic polymer, swelling the crosslinked dECM and synthetic polymer using one or more swelling solutions, thereby generating a hydrogel, selectively photo-crosslinking the swelled hydrogel using a patterned mask, seeding a plurality of cells onto the photo-crosslinked hydrogel, and culturing the cells on the pattern-photo-crosslinked hydrogel.

BRIEF DESCRIPTION OF THE DRAWINGS

The following detailed description of selected embodiments of the invention will be better understood when read in conjunction with the appended drawings. For the purpose of illustrating the invention, illustrative embodiments are shown in the drawings. It should be understood, however, that the invention is not limited to the precise arrangements and instrumentalities of the embodiments shown in the drawings.

FIG. 1**D depicts silver-stained SDS-PAGE results showing dark bands (high concentrations) for both dECM powder and clickable dECM in the stacking gel, indicating both contain large (>250 kDa) proteins. Clickable dECM produced a stronger band at <15 kDa, indicating that the treatment likely fragmented a portion of the dECM proteins into clickable dECM peptides.

FIG. 5**C depicts representative images of dual-reporter fibroblasts on soft and stiff hybrid-hydrogels on Day 7 and stiffened hybrid hydrogels on day 9 showing expression of Col1a1-GFP and αSMA-RFP Scale bar=25 μm.

DETAILED DESCRIPTION

Definitions

Figures 1A, 1B:
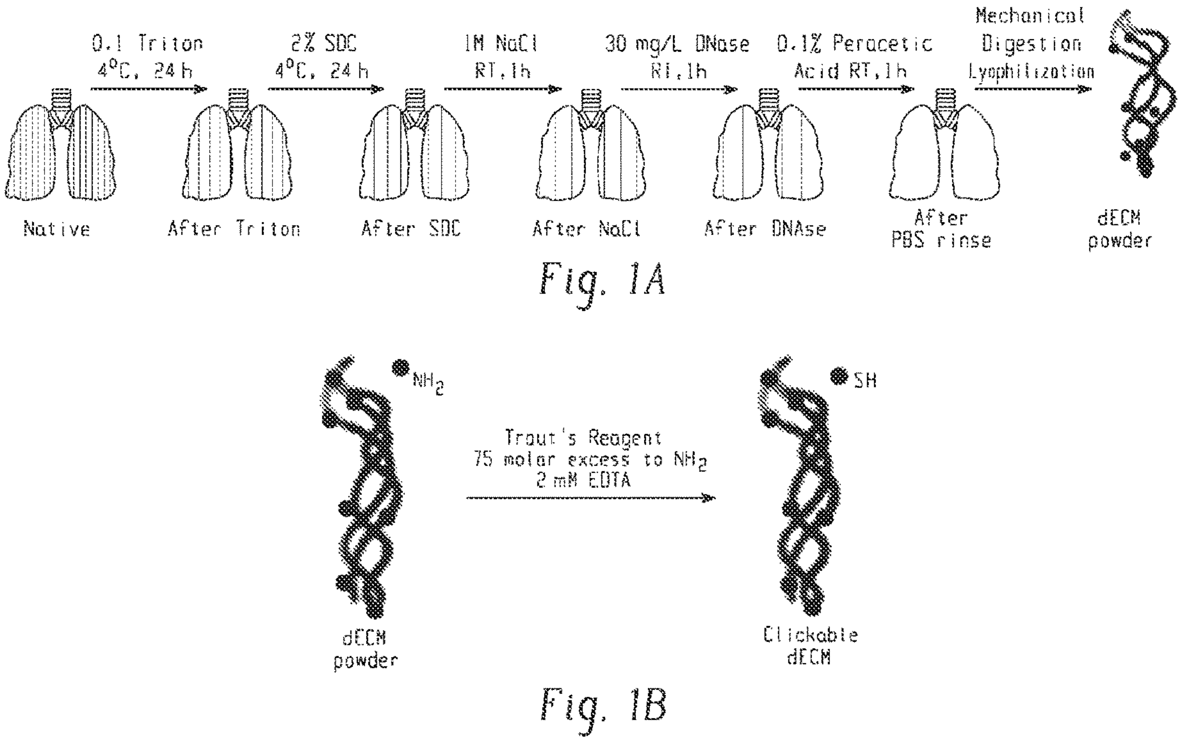
FIG. 1A depicts a schematic depicting the lung decellularization process. Briefly, native lungs are sequentially perfused with Triton X-100, sodium deoxycholate solution, DNAse solution and peracetic acid to remove all cellular components before being mechanically digested and lyophilized to form a powder.
FIG. 1B depicts decellularized porcine ECM that was treated with Traut's reagent at a 75-molar excess to primary amines ($NH_2$) and 2 mM EDTA to convert free primary amines to thiols creating a clickable decellularized extracellular matrix (dECM) crosslinker.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides hybrid hydrogel compositions and methods for generating hybrid hydrogels. The invention also proves systems and methods for evaluating the generation of a fibrotic phenotype in cells. The hybrid hydrogel compositions and systems of the present invention include one or more decellularized extracellular matrix (dECM) tissue crosslinked to one or more synthetic scaffolds. The crosslinked dECM-synthetic scaffold may have a patterned rigidity. In certain embodiments, the hybrid hydrogels of the disclosure combine a phototunable poly(ethylene glycol) (PEG) backbone with dECM from healthy or diseased tissue in a way that allows the decoupling of fibrotic (diseased) tissue composition (increased collagen) from subsequent changes in mechanical properties (increased elastic modulus) in a 3D system.

Hybrid Hydrogels

The present invention relates to hybrid hydrogel scaffolds including a decellularized extracellular matrix (dECM) tissue, and a synthetic polymer. The dECM may include any suitable tissue including for example, lung tissue, heart tissue, heart-lung block tissue, skin tissue, liver tissue, pancreatic tissue, kidney tissue, and the like. The tissue may include mammalian tissue, such as human tissue, porcine tissue, bovine tissue, equine tissue, murine tissue, rattus tissue, and the like. The dECM may be digested according to any suitable technique as understood in the art. For example, the dECM tissue may be detergent extracted, mechanically homogenized, and/or combinations thereof. The dECM may be modified using one or more techniques as understood in the art. For example, the dECM may undergo deamination, thiolation, and/or combinations thereof. The dECM may be functionalized with functional groups that can participate in one or more "click-chemistry" reactions with at least one degradable crosslinker. In other embodiments, the "click-chemistry" reaction is selected from, but not necessarily limited to, azide-alkyne cycloaddition, thiol-vinyl addition, thiol-yne, thiol-isocyanate, Michael addition, 1,3 dipolar cycloaddition, Diels-Alder addition and oxime/hydrazine formation. In some embodiments, the dECM may be functionalized with at least one functional moiety selected from the group consisting of acrylate, methacrylate, alpha-methacrylate, norbornene, thiol, azide, alkene, alkyne, oxime, hydrozone, isocyanate, tetrazine, maleimide, vinyl sulphone, dibenzocyclooctyne, one or more cyclooctynes, and NHS-esters.

The synthetic polymer may include one or more of poly(ethylene glycol), functionalized poly(ethylene glycol), poly(ethylene oxide), poly(vinyl alcohol), poly(vinyl acetate), poly(ethylene imine), polyacrylamide, poly(hydroxylethyl methacrylate), poly(N-vinyl pyrrolidone), poly (methacrylic acid), poly(butyl methacrylate), poly(methyl methacrylate), poly(meth acrylic acid), poly(N-isopropyl acrylamide), poly(hydroxylethylmethacrylate), acrylate-functionalized gelatin, methacrylate-functionalized poly (ethylene glycol), methacrylate-functionalized gelatin, acrylate-functionalized hyaluronic acid, and methacrylate-functionalized hyaluronic acid.

The synthetic polymer may be functionalized with at least one functional moiety that is acrylate, methacrylate, alpha-methacrylate, norbornene, thiol, azide, alkene, alkyne, oxime, hydrozone, isocyanate, tetrazine, maleimide, vinyl sulphone, dibenzocyclooctyne, or NHS-ester. In an embodiment, the synthetic polymer is functionalized with at least two, at least three, at least four, or at least eight functional moieties.

In an embodiment, the synthetic polymer comprises at least one functional moiety as described herein and further comprises a degradable linker group between the synthetic polymer and the at least one functional moiety. Exemplary degradable linker groups include enzyme-degradable, protease-degradable, photodegradable, and/or biodegradable groups. An exemplary enzyme-degradable group is a matrix metalloprotease (MMP) degradable group. In an embodiment, the photodegradable group is degraded through exposure to visible light (380 nm-760 nm) photoexcitation or ultraviolet (UV) light photoexcitation (100 nm-380 nm).

In an embodiment, the degradable linker group is an ortho-nitrobenzyl moiety, coumarin, azobenzene, rotaxane, aromatic disulfides, poly(glycerol sebacate) (PGS), polylactic-glycolic acid (PLGA), poly-lactic acid (PLA), poly-caprolactone (PCL), copolymers of polylactic-glycolic acid and poly-caprolactone (PCL-PLGA copolymer), copolymers of polyethylene glycol and poly-caprolactone (PEG-PCL copolymer), copolymers of polyethylene glycol and trimethylene carbonate (PEG-TMC copolymer), copolymers of polyethylene glycol and poly(glycerol sebacate) (PEG-PGS copolymer), copolymers of polylactic-glycolic acid and poly-lactic acid (PLGA-PLA copolymer), polyhydroxy-butyrate-valerate (PHBV), polyorthoester (POE), polyethylene oxide-butylene terephthalate (PEO-PBTP), poly-D,L-lactic acid-p-dioxanone-polyethylene glycol block copolymer (PLA-DX-PEG), spermine, 2,2'-(ethylenedioxy)bis(ethylamine) (EDBE), CGPQGIWGQGC peptide, GPQGIAGQ peptide (PCL-1), or IPVSLRSG peptide (PCL-2). The hybrid dECM-synthetic polymer hydrogel may be hydrated using one or more hydrating solutions as understood in the art. For example, the hybrid hydrogel may be hydrated using saline solution, one or more buffered saline solutions (e.g. PBS), cell culture media (e.g., Dulbecco's Modified Eagle Medium (DMEM), M199, and the like), one or more photosensitizer solutions, including, for example lithium phenyl-2,4,6-trimethylbenzoulphospinate (LAP), chlorins, bacteriochlorins, porphyrins including benzoporphyrins, phthalocyanines, prophycenes, hypericins, acetophenones, benzophenones, benzils and benzoins, thioxanthones, one or more inorganic peroxides, one or more azo compounds, and the like.

The hydrogel hybrid may have a tunable stiffness and/or elastic modulus. That is, the synthetic polymer may undergo crosslinking in order to modify its elastic modulus. For example, synthetic polymer of the hybrid hydrogel may be photo-crosslinked. The hybrid hydrogel may be selectively photo-crosslinked using for example, a mask, a discrete controlled beam photo wherein the light source only contacts selected regions of the synthetic polymer, or other suitable technique for selectively contacting the photoactivatable synthetic polymer with a light source. The light source may include a UV light source (e.g., light with a wavelength in the range of about 100 nm to 380 nm) such as a UV laser including a confocal microscopy laser. The light source may include a visible light source (e.g. light with a wavelength in the range of about 380 nm to about 760 nm). The mask may include any suitable mask as understood in the art. For example, the make may include a chrome-on-quartz photomask.

The synthetic polymer may be photo-tuned to have a patterned stiffness. The mask pattern may include any suitable pattern as contemplated in the art. For example, the mask pattern may include one or more shapes, arrays of shapes, concentric shapes or the like arranged in any suitable pattern as understood in the art. The shapes may include one or more circles, rings, squares, polygons, lines, or the like. The patterned shapes may be photo-crosslinked to have the same rigidity, variable rigidities, a gradient of rigidities, and/or combinations thereof. The rigidity may range of from about 1 Pa to about 10 Pa, about 10 Pa about 100 Pa, about 100 Pa to about 0.5 kPa, about 0.5 kPa to about 1 kPa, about 1 kPa to about 2 kPa, about 2 kPa to about 3 kPa, about 3 kPa to about 4 kPa, about 4 kPa to about 5 kPa, about 5 kPa to about 6 kPa, about 6 kPa to about 7 kPa, about 7 kPa to about 8 kPa, about 8 kPa to about 9 kPa, about 9 kPa to about 10 kPa, about 10 kPa to about 15 kPa, about 15 kPa about 20 kPa, about 20 kPa to about 25 kPa, about 25 kPa to about 50 kPa, about 50 kPa to about 75 kPa, about 75 kPa to about 100 kPa, or greater than about 100 kPa. The rigidity may include any and all subintervals of rigidities therebetween.

The hybrid hydrogel may be seeded with one or more cells or populations of cells. The cells may include vascular cells, lung cells, cardiac cells, muscle cells, neural cells, endocrine cells, paracrine cells bone cells, dermal cells, and the like. The cells may include fibroblasts, endothelial cells, epithelial cells, pericytes, osteocytes, neurocytes, and the like, and or one or more combinations thereof.

Methods

The present invention provides methods for generating one or more hybrid hydrogel as contemplated herein.

The methods may include preparing a functionalized dECM. The dECM may include decellularized tissue isolated from one or more tissue sources as contemplated herein, including for example, heart tissue, lung tissue, heart-lung block tissue, liver tissue, kidney tissue, pancreatic tissue, skin tissue, and the like. The dECM may be functionalized using any suitable techniques, including for example, by deamination, thiolation, or any other suitable technique or combination of techniques as contemplated herein. The dECM may be prepared as a "clickable" dECM as contemplated herein.

The methods may include preparing a synthetic polymer solution. The synthetic polymer solution may include one or of poly(ethylene glycol) functionalized poly(ethylene glycol), poly(ethylene oxide), poly(vinyl alcohol), poly(vinyl acetate), poly(ethylene imine), polyacrylamide, poly(hydroxylethyl methacrylate), poly(N-vinyl pyrrolidone), poly (methacrylic acid), poly(butyl methacrylate), poly(methyl methacrylate), poly(meth acrylic acid), poly(N-isopropyl acrylamide), poly(hydroxylethylmethacrylate), acrylate-functionalized gelatin, methacrylate-functionalized poly (ethylene glycol), methacrylate-functionalized gelatin, acrylate-functionalized hyaluronic acid, and methacrylate-functionalized hyaluronic acid.

The methods may include chemically crosslinking the dECM and the synthetic polymer. The dECM may be chemically crosslinked using any suitable crosslinking solution as understood in the art, include for example 1,4-Dithiothreitol (DTT).

The methods may include swelling the crosslinked dECM and synthetic polymer using one or more swelling solutions, thereby hydrating the hybrid hydrogel. The one or more swelling solutions may include one or more solutions as contemplated herein, including for example saline solution, buffered saline solution (e.g., phosphate buffered saline, Hank's buffered saline solution, and so forth), sterile water, cell culture medium (e.g., DMEM, M199, and the like).

The methods may include selectively photo-crosslinking the swelled hybrid hydrogel using a patterned mask as contemplated herein.

The methods may include seeding a population of cells onto the photo-crosslinked hydrogel. The population of cells may include one or more of a population of fibroblasts, endothelial cells, epithelial cells, pericytes, one or more precursor cells or stem cells, or pluripotent cells, as understood in the art, and one or more combinations thereof.

The present invention provides methods for evaluating the generation of fibrosis in a population of cells. The methods may include seeding a population of cells as described herein onto one or more hybrid hydrogels as described herein, culturing the cells for a duration of time, and evaluating the expression of fibrotic phenotypic markers in the cultured cells. For example, the cells may be cultured on or within the hybrid hydrogel for up to about 8 hours, about 8 hours to about 24 hours, about 1 day to about 2 days, about 2 days to about 3 days, about 3 days to about 5 days, about 5 days to about 7 days, about 7 days to about 9 days, about 9 day to about 10 days, about 10 days to about 20 days, about 20 days to about 30 day, about 30 days to about 40 day, about 40 days to about 50 days, about 50 days to about 60 days, about 60 days to about 70 days, about 70 days to about 80 days, about 80 days to about 90 days, about 90 days to about 100 days, or greater than about 100 days.

The cultured cells may be evaluated for expression of one or more phenotypic markers. The phenotypic markers may include one or more of collagen 1a1 (Col1a1), smooth muscle $\alpha$-actin ($\alpha$SMA), platelet-derived growth factor receptor-$\alpha$ (PDGFR$\alpha$), and the like. The one or more phenotypic markers may be detected using one or more suitable techniques as understood in the art including for example using one or more techniques such Western blot, ELISA, immunoprecipitation, immunofluorescence, detection of one or more fluorescent proteins, and the like. The cultured cells may be identified as being positive for fibrosis if the one or more phenotypic markers is detected at a level greater or lesser than a comparator control including a level of greater than up to 1.5-fold, about 1.5-fold, about 2-fold, about 2.5-fold, about 3-fold, or greater than about 3-fold.

EXPERIMENTAL EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Pathologic tissue remodeling is a hallmark of chronic fibrotic diseases caused by aberrant wound-healing. It is characterized by persistent and excessive production of biochemically abnormal extracellular matrix (ECM), resulting in spatially heterogeneous increases in tissue stiffness. Emerging evidence points toward pathologic ECM alterations and subsequent increases in local tissue stiffness as a driving force for the continuous alteration of cell phenotype and function.

Described herein is a strategy for synthesizing clickable dECM and combining it with a phototunable poly(ethylene glycol) (PEG) backbone in a way that allows the decoupling of fibrotic tissue composition from subsequent changes in mechanical properties to study the dynamic biological processes occurring in fibrosis. The novel hybrid-hydrogel system provides predictable control of initial substratum elasticity over a large range of moduli ($E=3.63\pm0.24$ to $13.35\pm0.83$ kPa) and facilitates spatiotemporal control over precise increases in local mechanical properties in situ. Using pulmonary fibrosis as an archetype of chronic fibrotic disease, primary platelet-derived growth factor receptor alpha-positive (PDGFR$\alpha$+) fibroblasts from the alveolar niche were isolated from adult dual-transgenic reporter mice that express green or red fluorescent protein in response to Collagen 1a1 (Col1a1) or $\alpha$SMA transgene expression, respectively, and used to monitor cellular responses to these new materials. PDGFR$\alpha$+ fibroblasts from the alveolar niche were selected for these assays because this is the proposed site of initial injury and remodeling in pulmonary fibrosis. Fibroblast activation was characterized by measuring expression of these transgenes in response to initial substrate modulus, dynamic stiffening ranging from healthy (E=1-5 kPa) to diseased levels (E>10 kPa), as well as patterns of alternating soft and stiff areas to mimic the effect of heterogeneous mechanical properties observed in fibrosis. The utility is demonstrated of this hybrid-hydrogel system for dynamically probing cell-matrix interactions with spatial control and this work highlights a new approach for understanding the biochemical and biophysical contributions to fibrotic disease progression.

Materials and Methods

Small Molecule and Macromer Synthesis

Synthesis of Ethyl 2-(Bromomethyl) Acrylate

Figure 7:
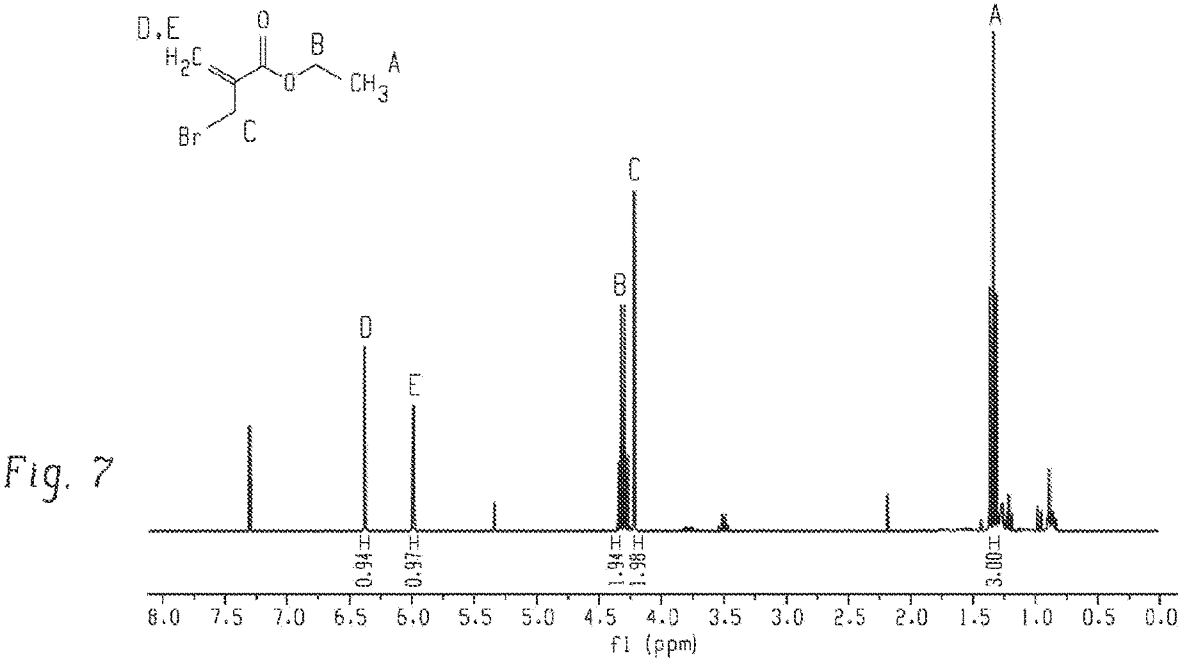
FIG. 7 depicts an exemplary $^1$H NMR spectrum of EBrMa ($CDCl_3$, 300 MHz). Percent functionalization was 97.6%. 1H-NMR (300 MHz, $CDCl_3$): δ (ppm) 1.3 (t, 3H, —$CH_3$), 4.16 (s, 2H, —$CH_2$—Br), 4.25 (q, 2H, —$CH_2$—O—), 5.9 and 6.3 (s, 1H, =$CH_2$).

Ethyl 2-(bromomethyl) acrylate (EBrMA) is commercially available but was synthesized following a previously published protocol. Briefly, 60 mmol ethyl 2-(hydroxymethyl) acrylate (EHMA; Sigma Aldrich) was dissolved in 60 ml diethyl ether in a round-bottom flask and 21 mmol phosphorous tribromide ($PBr_3$; Acros Organics) was slowly added while cooling the reaction vessel with an ice bath. Then, the mixture was warmed to room temperature and stirred for 3 hours to complete the reaction. Water (5 ml) was added to the mixture and it was extracted with hexane three times. The organic solutions from all three extractions were combined, washed with brine, and dried with anhydrous magnesium sulfate ($MgSO_4$; Fisher Scientific). The solvent was removed by rotary evaporation at 60° C. to give the final product at a 90% yield. The functionalization of the product was verified by proton NMR performed on a Bruker Advance-III 300 NMR Spectrometer (7.05 T) (FIG. 7). $^1H$-NMR (300 MHz, $CDCl_3$): δ (ppm) 1.3 (t, 3H, —$CH_3$), 4.16 (s, 2H, —$CH_2$—Br), 4.25 (q, 2H, —$CH_2$—O—), 5.9 and 6.3 (s, 1H, =$CH_2$).

Synthesis of Poly(Ethylene Glycol)-Alpha Methacrylate

Figure 8:
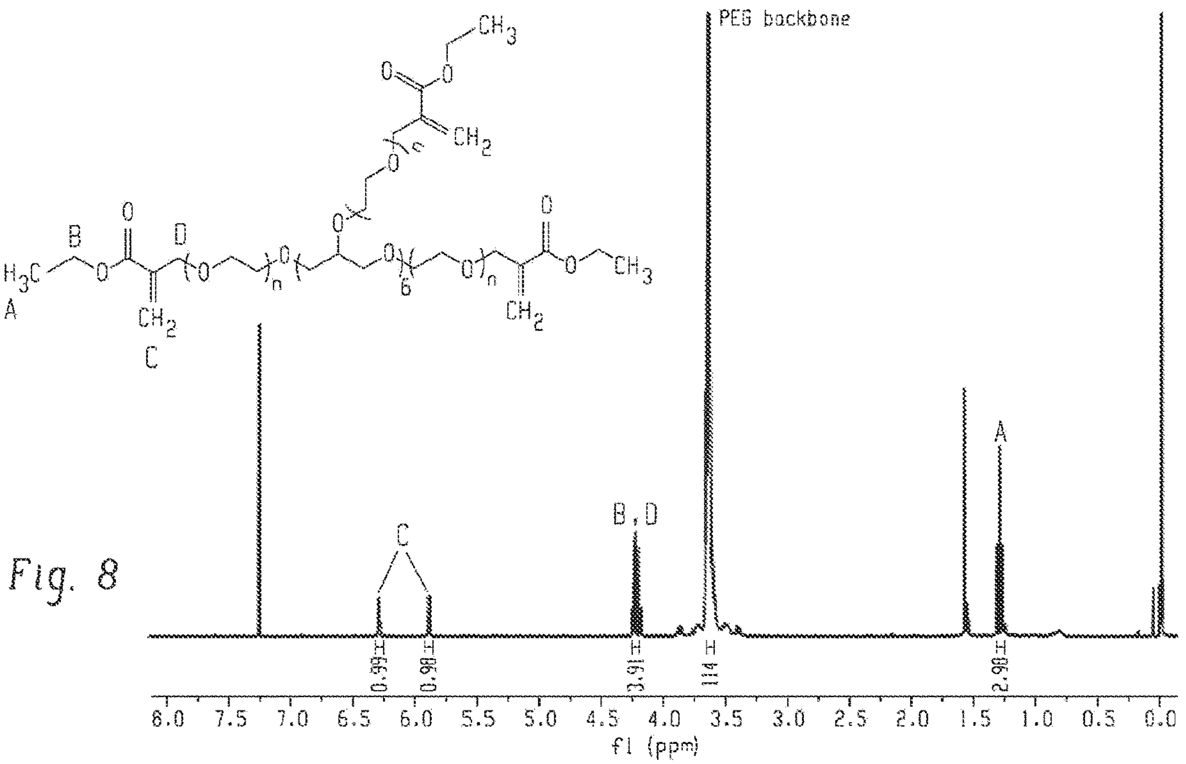
FIG. 8 depicts an exemplary $^1$H NMR spectrum of PEGαMA ($CDCl_3$, 300 MHz). The degree of vinyl end group, C=$CH_2$, calculated by the integration ratio of peak C (2H), compared to the peak of the PEG backbone. $^1$H NMR (300 MHz, $CDCl_3$): δ (ppm) 1.23 (t, 6H, $CH_3$—), 3.62 (s, 114H, PEG backbone), 4.17-4.21 (t, s, 8H, —$CH_2$—C(O)—O—O, —O—$CH_2$—C(=$CH_2$)—), 5.90 (s, 1H, —C=$CH_2$), 6.31 (s, 1H, —C=$CH_2$).

Poly(ethylene glycol)-hydroxyl (PEG-OH; 8-arm, 10 kg/mol; JenKem Technology) was dissolved in anhydrous tetrahydrofuran (THF: Sigma Aldrich) in a round-bottom flask and purged with argon. Sodium hydride (NaH; Sigma Aldrich) was injected through a septum into the reaction vessel at 3X molar excess to PEG-hydroxyl groups. EBrMA was added drop-wise using an addition funnel at a 6× molar ratio to PEG-OH groups, and the reaction was stirred at room temperature for 72 hours protected from light. The mixture was neutralized with 1 N acetic acid until gas evolution ceased and filtered through Celite 545. The solution was concentrated by rotary evaporation at 60° C., precipitated dropwise into in ice-cold diethyl ether and washed three times in diethyl ether. The solid product was then dried under vacuum overnight. The product was purified using dialysis (1 kg/mol MWCO, ThermoFisher) for four days, and then flash frozen in liquid nitrogen and lyophilized to give the final product. The functionalization of the product was verified by proton NMR (FIG. 8). $^1H$ NMR (300 MHz, $CDCl_3$): δ (ppm) 1.23 (t, 6H, $CH_3$—), 3.62 (s, 114H, PEG backbone), 4.17-4.21 (t, s, 8H, —$CH_2$—C(O)—O—O, —O—$CH_2$—C(=$CH_2$)—), 5.90 (s, 1H, —C=$CH_2$), 6.31 (s, 1H, —C=$CH_2$).

Synthesis of Poly(Ethylene Glycol)-Methacrylate

Figure 9:
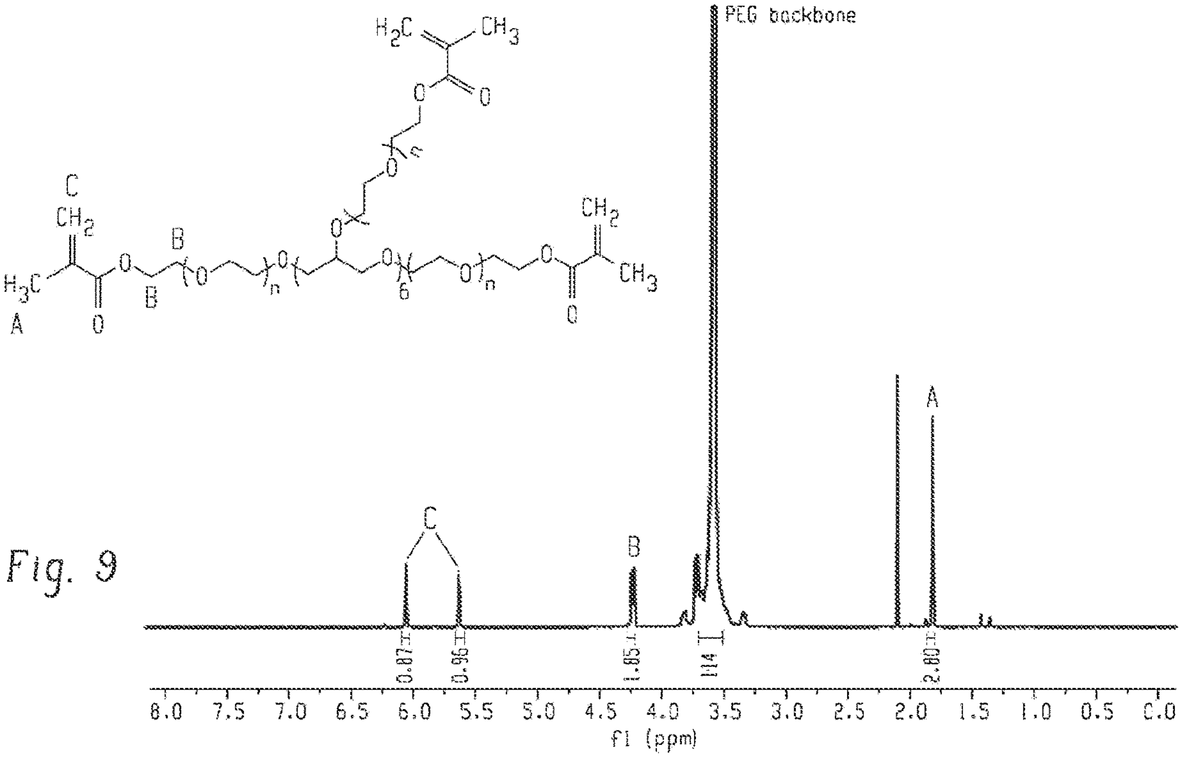
FIG. 9 depicts an exemplary $^1$H NMR spectrum of PEGMA ($CDCl_3$, 300 MHz). The degree of vinyl end group, C=$CH_2$, calculated by the integration ratio of peak C (2H), compared to the peak of the PEG backbone was found to be 91%. $^1$H NMR (300 MHz, $CDCl_3$): δ (ppm) 1.23 (t, 6H, $CH_3$—), 3.62 (s, 114H, PEG backbone), 4.17-4.21 (t, s, 8H, —$CH_2$—C(O)—O—O, —O—$CH_2$—C(=$CH_2$)—), 5.90 (s, 1H, —C=$CH_2$), 6.31 (s, 1H, —C=$CH_2$).

This protocol was adapted from a previously reported version. PEG-hydroxyl (8-arm, 10 kg/mol; JenKem Technology) was dissolved in anhydrous tetrahydrofuran (THF; Sigma Aldrich) and purged with argon. Triethylamine (4 equivalents with respect to hydroxyls, TEA; Thomas Scientific) was injected through a septum into the reaction vessel at 4× molar excess to PEG-hydroxyl groups. Then, methacryloyl chloride (Acros Organics) was added dropwise at 4× molar excess with respect to hydroxyls, and the reaction was stirred for 48 h at room temperature before being filtered through Celite 545 to remove quaternary ammonium salts. The solution was then concentrated by rotary evaporation and precipitated and washed 3× in ice-cold diethyl ether. The product was dried under vacuum overnight. The product was verified by proton NMR (FIG. 9). $^1H$ NMR (300 MHz, $CDCl_3$): δ (ppm) 1.8 (t, 3H, $CH_3$—), 3.62 (s, 114H, PEG backbone), 4.17-4.21 (m, 2H, —$CH_2$—C(O)—O—O) 5.60 (t, 1H, —C=$CH_2$), 6.0 (d, 1H, —C=$CH_2$).

ECM Decellularization and Thiolation

ECM Decellularization

Decellularization was performed as follows. Briefly, the heart-lung block was removed from the thoracic cavity and incubated in deionized (DI) water on ice. The lungs were sequentially perfused through the trachea/main bronchus and pulmonary artery/main vessel with a perfusion pump at 1-3 l/min with a DI water solution containing 5× penicillin/streptomycin (PS), 0.1% Triton X-100 solution, 2% sodium deoxycholate, 1 M sodium chloride, 30 μg/ml DNAse, and 0.1% peracetic acid in 4% ethanol to remove all cellular components (FIG. 1A). Finally, the tissue was homogenized and lyophilized to form a powder. Sufficient decellularization was confirmed through hematoxylin and eosin staining of the decellularized lung tissue, quantification of dsDNA by Quant-iT™ PicoGreen™ dsDNA Assay Kit (ThermoFisher Scientific), and analysis of residual DNA fragments by gel electrophoresis.

dECM Thiolation

To create a clickable, decellularized ECM (dECM) crosslinker, the free primary amines on the dECM were converted into thiol moieties using 2-iminothiolane hydrochloride (Traut's reagent; Sigma Aldrich) (FIG. 1B). The primary amine concentration was measured using a ninhydrin (NHN: Sigma Aldrich) assay according to the manufacturer's protocol. Next, the dECM was reacted with a 75-molar excess Traut's reagent to primary amine concentration with 2 mM ethylenediaminetetraaetic acid (EDTA; Thermofisher) for 2 hours at room temperature. Following this reaction, the solution was filtered through Zeba Spin Desalting Columns (7 kg/mol MWCO, 10 ml; ThermoFisher) to remove the Traut's reagent. The final solution was lyophilized and the number of thiol groups that were introduced to the dECM was quantified using Ellman's reagent (5,5'dithio-bis-(2-nitrobenzoic acid) or DTNB; Sigma Aldrich) according to manufacturer's protocol.

A Pierce™ Silver Stain Kit (Thermo Fisher Scientific) was used to qualitatively analyze protein size distribution in dECM compared to thiolated-dECM. Lyophilized dECM and thiolated-dECM were lysed in RIPA buffer and loaded into sodium dodecyl sulfate-polyacrylamide gel electrophoresis (SDS-PAGE) gels. After resolving the protein by size, the gels were silver stained according to the manufacturer's protocol to visual and the molecular weight of dECM proteins, peptides and fragments before and after thiolation.

Additional dECM thiolation studies are described in Example 3.

Hydrogel Formation

The thiol-functionalized dECM (clickable dECM) and 1,4-Dithiothreitol (DTT: Acros Organics) crosslinkers were reacted with PEGαMA in a Michael addition reaction off-stoichiometry at a 3:8 thiol to αMA ratio. The hydrogel formulation was optimized by varying the percentage of DTT to clickable dECM in order to achieve a desired elastic modulus. The clickable dECM was dissolved in 15 mM solution of Tris(2-carboxyethyl)phosphine hydrochloride (TCEP; Fisher Scientific) for 1 hour at a 20× molar ratio to the thiol concentration as determined by the Ellman's assay. Stock solutions of PEGαMA (0.4 mg/μl), DTT (500 mM), and a peptide sequence that mimics adhesive ligands (0.2 mM; CGRGDS; GL Biochem) were prepared in 0.3 M, pH 8 4-(2-hydroxyethyl)-1piperazineethanesulfonic acid buffering agent (HEPES; Life Technologies). A precursor solution was made by combining the clickable dECM, DTT, CGRGDS and then adding the PEGαMA at 15 wt %. Hydrogels were polymerized by placing 40 μl drops of the precursor solution between two hydrophobic glass slides treated with SigmaCote (Sigma Aldrich). The reaction proceeded for one hour at 37° C. Hydrogels were equilibrated in PBS at 4° C., with or without 2.2 mM photo-initiator lithium phenyl-2,4,6-trimethylbenzoulphospinate (LAP) for 24 hours. Hydrogels swollen in LAP were exposed to light (365 nm light, $mW/cm^2$) for 5 minutes using an OmniCure Series 2000 UV lamp (Lumen Dynamics) to create stiff hybrid-hydrogel samples. For cell experiments, the hydrogel-forming stock solutions were dissolved in sterile HEPES and the precursor solution was made from the resulting stocks under aseptic conditions. Glass coverslips (18 mm; Fisher Scientific) were silanated with (3-aminopropyl) trimethoxysilane (ATS; Sigma) using a liquid deposition technique. Hydrogel precursors were deposited in 90 μl drops between hydrophobic glass slides and silanated cover slips for 1 hour at 37° C. Hydrogels were then swollen in complete medium (DMEM/F12; Gibco) supplemented with 100 U/ml penicillin, 100 μg/ml streptomycin and 2.5 μg/ml amphotericin B (Life Technologies), and 10% fetal bovine serum (FBS; ThermoFisher) with or without 2.2 mM LAP for 24 hours at 37° C. prior to stiffening or use as soft hybrid-hydrogel samples in experiments.

Characterization of Hybrid-Hydrogel Network Formation

Rheology was used to assess the mechanical properties of the hydrogels following gelation. Hydrogel samples (height=300 μm; diameter=8 mm) were loaded onto a Discovery HR2 rheometer (TA Instruments) with an 8-mm parallel plate geometry and the Peltier plate set at 37° C. The geometry was lowered until the instrument read 0.03 N axial force, and the gap distance was noted. The gap distance between the plate and the geometry was adjusted until the storage modulus measurement (G') plateaued and a percent compression of the specific hydrogel was defined and used moving forward. The samples were subjected to frequency oscillatory strain with a frequency range of 0.1 to 100 rad/s at 1% strain. The elastic modulus (E) was calculated using rubber elastic theory, assuming a Poisson's ratio of 0.5 for bulk measurements of elastic hydrogel polymer networks.

Hybrid-hydrogel morphology was visualized by scanning electron microscopy (SEM). Briefly, soft and stiffened hybrid-hydrogels were frozen at −80° C. for 2 hours and lyophilized at −80° C. for 24 hours (Freezone 4.5, Labconco, US). Samples were subsequently sputter-coated with 2 nm platinum/palladium (80/20) in a Quorum Q150T ES turbo pumped sputter coater and examined with the secondary electron detector at 1.5 kV in a Jeol JSM-7800F FEG-SEM.

Distribution of the clickable dECM and the PEG backbone components within hybrid-hydrogels was visualized via confocal microscopy. Clickable dECM crosslinker was treated with TCEP for 1 h as described above. AlexaFluorm 647 $C_2$ Maleimide (ThermoFisher) at 0.8 mM was added to this solution and allowed to react for 2 h to conjugate the dye to the thiols on the crosslinker. Hybrid-hydrogels were polymerized by placing a 40 μL drop of the precursor solution containing the labeled dECM crosslinker on a silanated glass slide and allowing the reaction to proceed for 1 h at 37° C. The PEG component of these hybrid-hydrogel samples was visualized through immunostaining. Briefly, samples were blocked with 5% bovine serum albumin (BSA; ThermoFisher) for 1 h. Recombinant anti-PEG antibody produced in rabbit (ab170969: abcam) was diluted 1:10 in an immunotluorescence (IF) solution containing 3% v/v BSA with 0.1% v/v Tween 20 (Sigma) in PBS. Samples were incubated with the primary antibody solution overnight at 4° C. After washing three times with IF solution, the hybrid-hydrogels were incubated with goat-anti-rabbit IgG Alexa Fluor-488 secondary antibody (1:200 in IF solution, ThermoFisher) overnight at 4° C. Samples were rinsed with PBS three times and imaged on a Zeiss LSM780 confocal microscope.

Hydrolytic Stability

Hybrid-hydrogels and fully synthetic 17 wt % poly(ethylene glycol)-methacrylate (PEGMA; 10 kg/mol) crosslinked with 100% DTT were fabricated, swollen in 2.2 mM LAP, stiffened by exposure to light (365 nm light, 10 $mW/cm^2$) for 5 minutes (OmniCure Series 2000; Lumen Dynamics), and monitored every ten days for up to 60 days. Two assays were performed on each condition at every timepoint to examine the hydrolytic stability of the two types of hydrogels. Rheology was completed as described above and then each sample was placed in DI water, lyophilized and weighed to record the dry polymer mass.

Spatial Patterning of Hybrid-Hydrogel Modulus

Hydrogels were fabricated as described above for cell experiments and swollen in (DMEM/F12; Gibco) supplemented with 100 U/ml penicillin, 100 μg/ml streptomycin and 2.5 μg/ml amphotericin B (Life Technologies), 1% FBS (ThermoFisher), 2.2 mM LAP, and 10 μM methacryloxyethyl thiocarbamoyl rhodamine B (Polysciences Inc). Hybrid-hydrogels were exposed to 365 nm light at 10 $mW/cm^2$ through a chrome-on-quartz photomask to spatially pattern defined regions of increased elastic modulus. Two line patterns were produced with either 50- or 100-micron width and spacing.

Equilibrium Swelling Ratio

Hybrid-hydrogel network formation was further characterized by measuring and calculating the experimental volumetric swelling ratio. Soft and stiffened hybrid-hydrogels were allowed to swell in phosphate buffered saline (PBS) and the swollen mass of n=4 replicates was measured at 1, 2, 6, 24, and 48-hour time points. The hydrogels were then placed in deionized water and lyophilized in order to record the dry polymer mass. The volumetric swelling ratio (Q) was calculated using equation (1)

$$Q=1+\rho_{PEG}/\rho_{solvent}(M_s/M_d-1) \quad \text{Equation(1)}$$

where $\rho_{PEG}$ is the polymer density, $\rho_{solvent}$ is the solvent density, $M_s$ is the swollen mass of the hydrogel and $M_d$ is the dry mass.

Primary Cell Isolation

Male and female, 8-12-week-old, dual-transgenic reporter C57BL/6J mice were bred for this study. Fibroblasts from this GFP-Col1a1×RFP-αSMA strain express green fluorescent protein (GFP) or red fluorescent protein (RFP) transgenes upon the expression of Col 1a1 and αSMA promoters, respectively. Non reporter (GFP−, RFP−) C57BL/6J mice (8-12-weeks-old), which resulted from the breeding protocol were used for cell viability experiments.

Cells isolated from enzymatically dispersed whole lung were sorted using magnetic microbeads that were conjugated with specific monoclonal antibodies in order to purify a PDGFRα-positive fibroblast population, as follows. At the time of animal sacrifice, the heart-lung block was collected. The lungs were filled with mom temperature dispase solution (5 U/ml; Life Technologies) and allowed to collapse before infusing with 1% low melt agarose (LMP Ultrapure; Life Technologies) and placing in iced PBS. The lungs were transferred to dispase solution and incubated for 45 minutes at room temperature. Then, the lungs were transferred to complete DMEM with high glucose (Life Technologies) supplemented with 100 U/ml penicillin, 100 μg/ml streptomycin and 2.5 μg/ml amphotericin B (Life Technologies), and 10% FBS (ThermoFisher) with DNAse solution (0.33 U/ml; Life Technologies) in GentleMACS C tubes (Miltenyi Biotec, Inc) at a final volume of 3 ml of digestion mix. The lungs were digested using a GentleMACS Dissociator (Miltenyi Biotec, Inc) on the lung setting 1 and 2 (275 RPM for 37 seconds and 3300 RPM for 38 seconds respectively), and then filtered using a 40-μm cell strainer, centrifuged to remove the supernatant and resuspended in complete medium to count. The solution was centrifuged to remove the supernatant before resuspending in buffer consisting of 0.5% bovine serum albumin (BSA) and 2 mM EDTA in PBS (PEB buffer). Magnetic microbeads conjugated to monoclonal anti-mouse CD31 and to monoclonal anti-mouse CD45 antibodies (Miltenyi Biotec, Inc.) were added to the solution to magnetically label the mature endothelial cells and leukocytes respectively. The solution was triturated twice to mix and incubated at 4° C. for 15 minutes. The cells were then washed with PEB buffer, centrifuged and resuspended in 500 μl PEB buffer before being applied to LS Columns (Miltenyi Biotec, Inc.) and placed in the magnetic field of a Quadromacs Separator (Miltenyi Biotec, Inc). The columns were rinsed with 9 ml, cells that passed through the columns in this step were the CD45−/CD31− fraction and the CD45+/CD31+ cell fraction was discarded. The CD45−/CD31− fraction was counted, centrifuged to remove the supernatant, resuspended in buffer and sorted for PDGFRα+ fibroblasts using microbeads conjugated with anti-CD140a (Miltenyi Biotec, Inc). This cell suspension was loaded into a new column, placed into the magnetic field, and rinsed to remove unlabeled cells. The column was finally removed from the magnetic separator and immediately flushed into a 50 ml conical tube using PEB buffer solution. This resulting solution contained the desired cell fraction (CD45−, CD31−, and CD140a+).

Cellular Viability

Sorted PDGFRα+ fibroblasts from non-reporter mice were seeded onto n=6 soft and stiff hybrid-hydrogels at a density of 10,000 cells/cm$^2$ and cultured in complete medium (DMEM/F12 supplemented with 100 U/ml penicillin, 100μ/ml streptomycin and 2.5 μg/ml amphotericin B (Life Technologies), and 10% FBS (ThermoFisher)). Samples were incubated with 10% v/v PrestoBlue™ Cell Viability Reagent (ThermoFisher) in culture medium for 3 h in a humidified incubator (37° C., 5% $CO_2$) on Days 1, 3, 5, 7, and 9. Three aliquots of the media containing viability reagent were then transferred to a 96-well plate and read on a plate reader (540 nm excitation, 600 nm emission; Synergy H1 Hybrid Multi Mode Reader; BioTek). Average fluorescence intensity values for all conditions at each time point were normalized to the respective readings acquired on Day 1 to calculate normalized metabolic activity.

Cells seeded onto soft, stiff and stiffened surfaces using the same procedure were stained with 1 mM calcein-AM (ThermoFisher) diluted 1:3000 in media to visualize live cells and 2 μg/ml molecular probe Hoechst 33342, Trihydrochloride, Trihydrate (Tocris) to stain cell nuclei and incubated for 30 minutes at 37° C. The cells were then rinsed with PBS and imaged. Cells stained by both calcein-AM and Hoechst were determined to be alive, while cells only stained by Hoechst were determined to be dead.

Cellular Activation

Figures 5A, 5B, 5C:
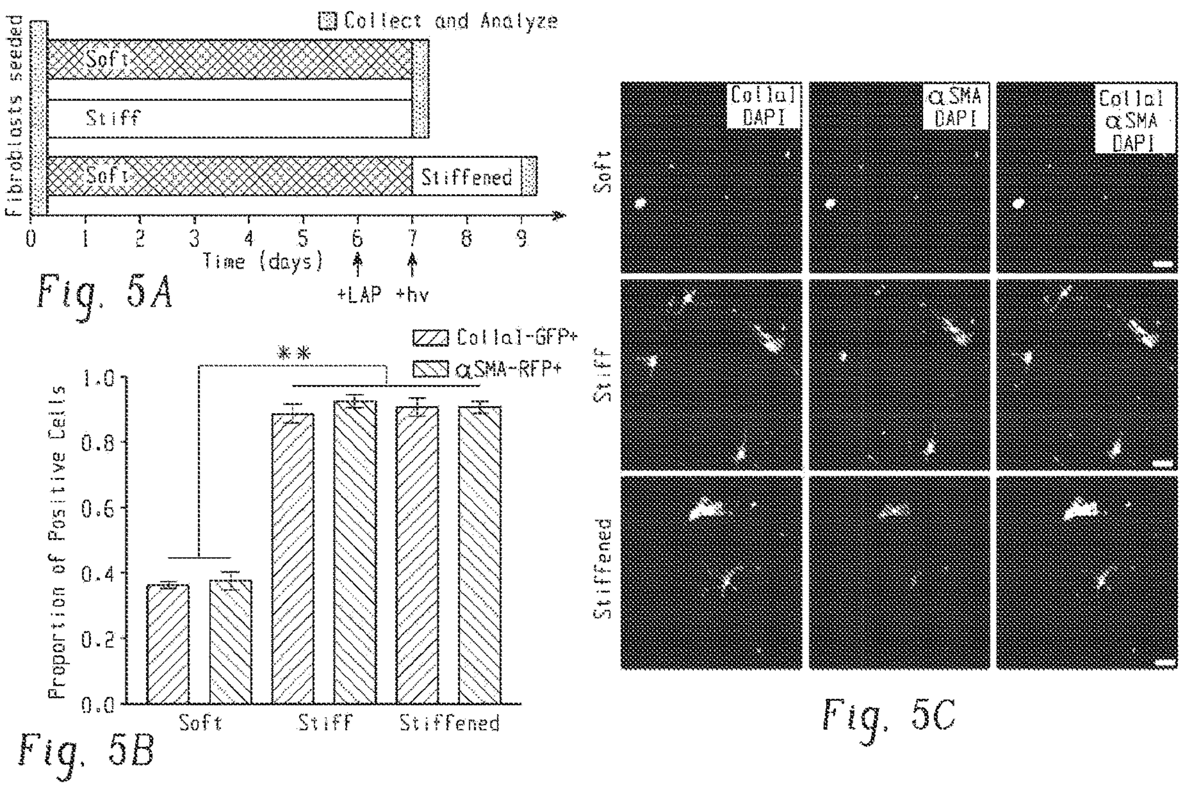
FIG. 5A depicts a schematic of the timeline for temporal stiffening during activation experiments. Gray and dark blue bars indicate the culturing time of dual-reporter fibroblasts on soft and stiff substrates, respectively. Cells were cultured in 1% FBS media for all conditions. The photoinitiator (LAP) was added to culture media on day 6 for hydrogels to be stiffened, and 365 nm UV light at 10 mW/$cm^2$ (hv) was applied for 5 minutes at day 7. Pink lines represent when samples were collected and analyzed.
FIG. 5B depicts the average proportion of dual-reporter fibroblasts that positively expressed Col1a1-GFP (green) and αSMA-RFP (red) for soft, stiff and stiffened conditions (n=6, mean±SEM). Significantly more cells cultured on stiff and stiffened substrates expressed Col1a1-GFP and αSMA-RFP than those cultured on soft substrates. (ANOVA, Tukey Test, : p<0.0001).

PDGFRα+ fibroblasts from dual-reporter (GFP-Coll a1×RFP-αSMA) mice (8-12 weeks old) were seeded onto soft or stiff hydrogels at a density of 10,000 cells/cm$^2$ and cultured in medium (DMEM/F12 supplemented with 100 U/ml penicillin, 100μ/ml streptomycin and 2.5 μg/ml amphotericin B, and 1% FBS). All hydrogels were incubated in a humidified incubator (37° C., 5% $CO_2$). On Day 6, the cell culture medium was replaced with complete medium containing 2.2 mM LAP photo-initiator on n=4 soft hydrogel samples. The following day (day 7) n=4 soft and stiff hydrogels were collected for analysis and the soft hydrogels treated with LAP were stiffened by exposure to cytocompatible 365 nm light at 10 mW/cm$^2$ for 5 minutes, rinsed three times to remove any residual LAP, and incubated (37° C., 5% $CO_2$) for two more days before being collected for analysis on Day 9 (FIG. 5A). This process was repeated for a total of three biological replicates. All samples were rinsed with PBS, fixed with 4% v/v paraformaldehyde (Electron Microscopy Sciences) in PBS for 30 minutes at room temperature and quenched with 100 mM glycine (Sigma) in PBS for 15 minutes at room temperature. Following fixation cells were rinsed with PBS, permeabilized with 0.2% Triton X-100 for 10 minutes at room temperature, and then stained with DAPI (1:10,000, Sigma) for 15 minutes at room temperature. Finally, samples were washed with PBS and mounted using Prolong Gold Antifade reagent (ThermoFisher) to preserve for imaging.

Spatial Control Over Cellular Activation

Sorted PDGFRt+ dual-reporter fibroblasts were seeded onto patterned hydrogels (n=6) at a cell density of 15,000 cells/cm$^2$ and cultured with in medium supplemented with 1% FBS. Samples were incubated in a humidified incubator (37° C., 5% $CO_2$) for seven days and then collected and prepared for analysis as described above.

Fluorescence Microscopy and Image Analysis

All microscopy was performed using an upright, epifluorescent microscope (BX-63, Olympus). Ten fields of view were randomly selected and imaged on each sample at 10× magnification. Image analysis for activation experiments was performed using ImageJ software to count cells positive for GFP-Col1a1 and/or RFP-oSMA. These cell counts were divided by the total cell number acquired by counting DAPI-positive nuclei to calculate the proportion of GFP-Coll a1-positive and RFP-αSMA-positive cells on each sample.

Statistical Analysis

All quantitative hydrogel characterization was performed with a minimum of n=3 technical replicates. All in vitro experimental studies involving cell culture were performed with n=4 technical replicates in biological triplicate. Data were presented as mean±standard error of the mean (SEM) or 95% confidence interval as described in each figure caption. GraphPad Prism 8 Software was used to perform all statistical analyses. One-way analysis of variance (ANOVA) with Tukey's post-hoc multiple comparisons tests were done on each experimental measure with multiple groups for pairwise comparisons among conditions with a 95% confidence interval. A 2-tailed Student's T-test was used when comparing fewer than three groups. P-values of <0.05 were considered significant and designated on plots as *<0.05 or **<0.0001. Linear regression analysis with a 95% confidence interval was completed to compare trends over time.

Results and Discussion

Hybrid-Hydrogel Formation and Characterization

Advances in lung decellularization techniques have fueled a growing interest in biomaterials from dECM. For example, a protocol for fabricating hydrogels derived from porcine lung dECM has been reported that supported mesenchymal stem cell culture in vitro and delivery to the pulmonary system in vivo. While these materials comprise the complex biochemical cues that cells encounter in vivo, they are limited by poor mechanical properties (E~30 to 120 Pa) that do not recapitulate healthy or diseased lung tissue. To overcome this limitation and decouple dECM composition from mechanical properties others have coated polyacrylamide-based hydrogels of modulus values ranging from 1.8 kPa to 23.7 kPa with healthy and fibrotic human-lung dECM. The results of these studies demonstrated that changes in αSMA expression and organization were mechanosensitive regardless of composition. In another study, dECM was methacrylated and covalently crosslinked with gelatin methacrylamide to form 3D hydrogels with elastic modulus values ranging from approximately 12 kPa to 66 kPa. While these experiments were certainly a breakthrough in modeling fibrotic disease in vitro, these static systems do not reproduce the spatiotemporal microenvironmental changes that occur during fibrotic disease progression and have been implicated as a major driver of cellular activation and disease progression.

Figures 1C, 1D:
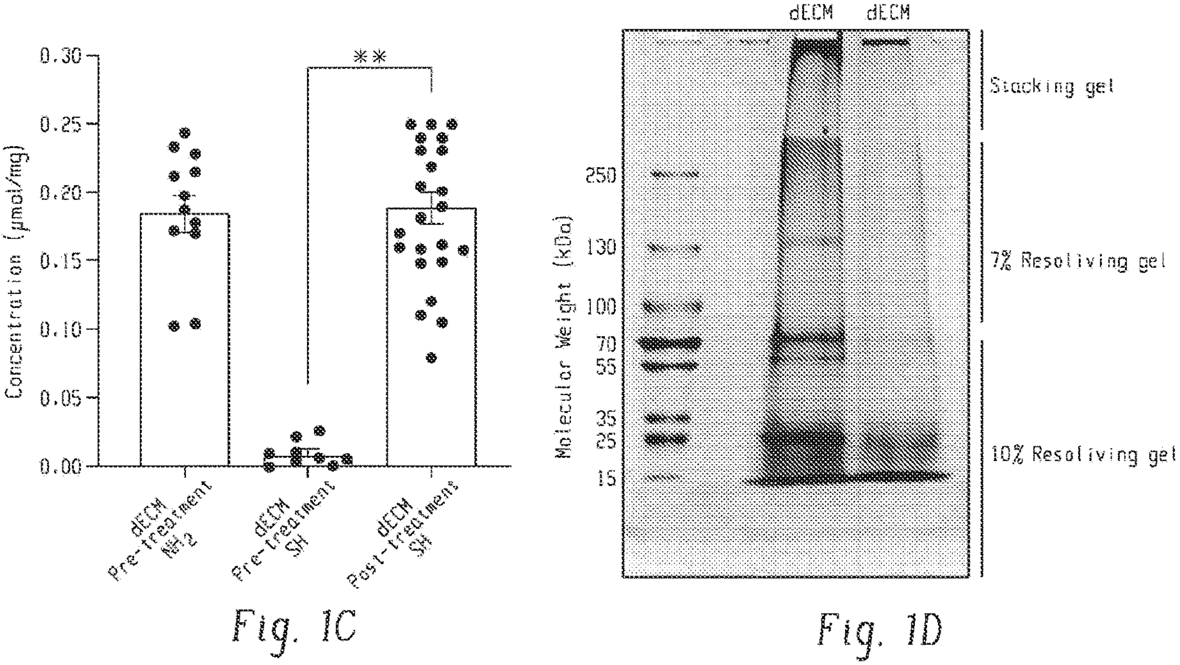
FIG. 1C demonstrates that a significant increase in thiol concentration was measured post-treatment using an Ellman's assay (5,5'-dithio-bis-(2-nitrobenzoic acid). (N=6, : pr0.0001, ANOVA, Tukey test).

The present disclosure relates in part to a method for synthesizing a clickable dECM crosslinker that facilitates a dual-stage polymerization reaction providing dynamic control over matrix mechanical properties in real time that can be implemented in 3D. First, porcine lungs were decellularized using an established protocol (FIG. 1A). Clickable dECM was generated by converting the naturally occurring primary amines on native dECM to yield thiol moieties with Traut's reagent (FIG. 1B) The average primary amine concentration of porcine dECM pre-treatment was measured to be 0.184±0.0135 μmol/mg by a Ninhydrin assay. The average thiol concentration measured by Ellman's assay before treatment with Traut's reagent was extremely low (0.00753±0.0273 μmol/mg) and increased significantly to 0.189±0.0117 μmol/mg ($p<0.05$, Tukey Test) (FIG. 1C). This value was not statistically different from the initial primary amine concentration and indicated nearly complete conversion.

Traut's reagent has been used extensively to thiolate natural polymers and growth factors, but the impact of this reaction on dECM is not yet well understood. Therefore, it was investigated whether the thiolation process induced degradation of dECM molecules. As may conventional protein measurement techniques rely on the detection on amines, we performed silver staining of dECM pre and post-thiolation on SDS-PAGE gels. Silver staining is a commonly used protein detection technique with high sensitivity which relies on the binding of silver ions to the negative side chain of proteins, and thus avoids potential interference due to thiolation of amine groups. Silver staining of dECM before thiolation revealed a wide distribution of proteins from >15 kDa to some above 250 kDa. In contrast, a loss of high molecular weight proteins (>250 kDa) and an increase in proteins<15 kDa was observed following thiolation, indicating that that the treatment likely cleaved a portion of the dECM proteins into clickable dECM peptides (FIG. 1D).

Figures 2A, 2B, 2C:
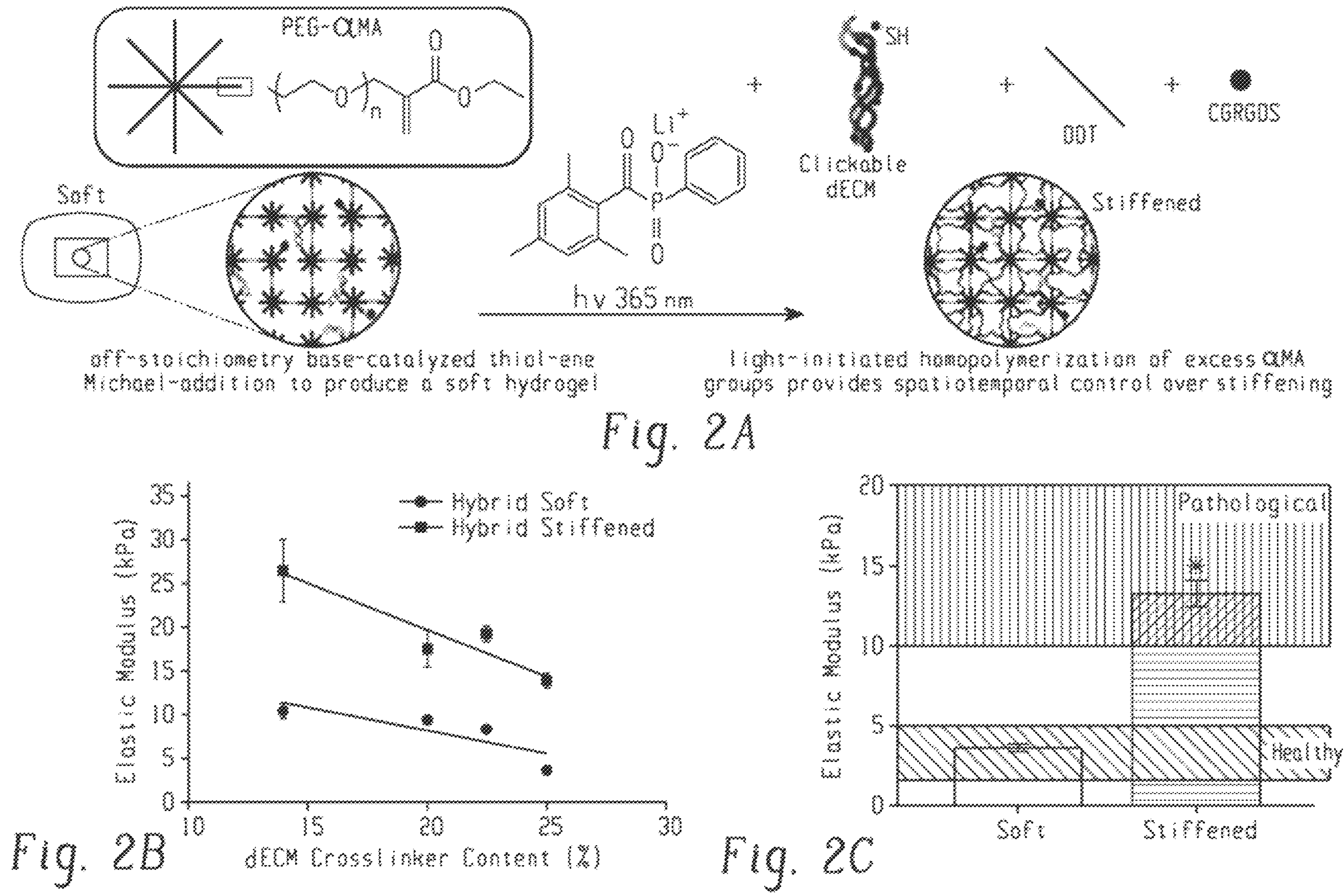
FIG. 2A depicts a schematic of the dual-stage polymerization reaction that combines PEGαMA and the clickable dECM crosslinker with DTT and CGRGDS to enable spatiotemporal control over stiffening.
FIG. 2B demonstrates that the elastic modulus of soft and stiffened hybrid hydrogels decreased with increasing dECM content ranging from 14% to 25% dECM (n=4, mean±SEM).
FIG. 2C depicts hybrid hydrogel formulations were adjusted so that soft and stiffened samples resulted in elastic modulus values within healthy and pathologic ranges, respectively (n=4, mean±SEM, *: $p<0.05$, ANOVA, Tukey test).
Figure 10:
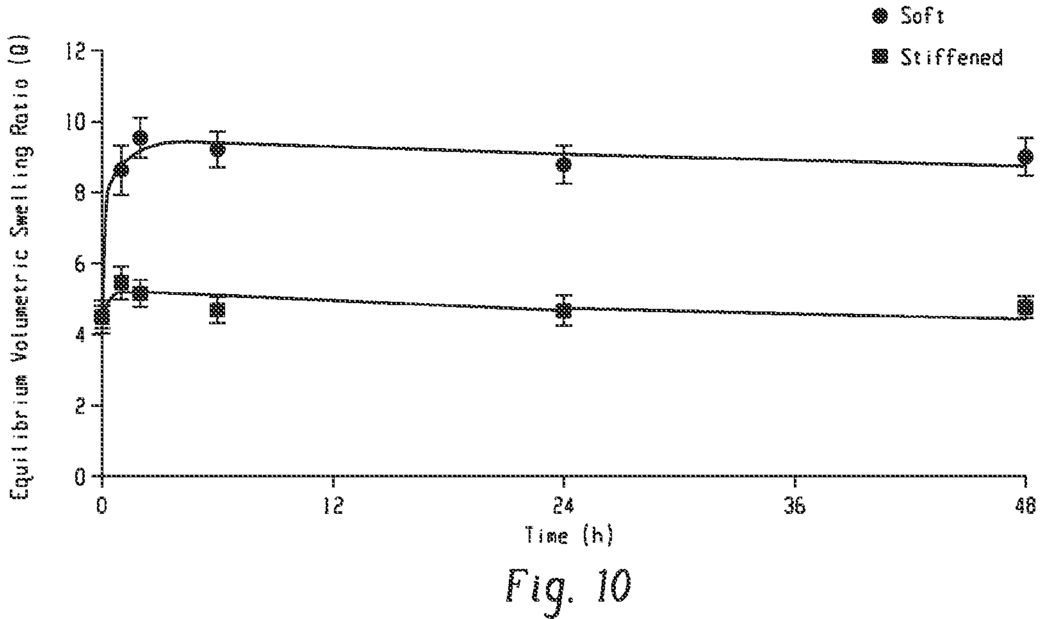
FIG. 10 depicts experimental equilibrium volumetric swelling ratio (Q) calculations that revealed that both soft and stiffened hybrid-hydrogels reached an equilibrium value within 6 hours of swelling in PBS. The equilibrium volumetric swelling ratio of the soft hybrid-hydrogel was approximately two times higher than the stiffened hybrid-hydrogel indicating differences in crosslinking density.

To demonstrate the versatility of this clickable dECM crosslinker, it was incorporated into a PEGαMA-based stiffening hybrid-hydrogel system. First, clickable dECM was reacted off-stoichiometry with DTT and a peptide sequence mimicking a binding region on the basement membrane protein fibonectin (CGRGDS) through a thiol-ene Michael addition reaction. This thiol-ene polymerization proceeded by a "click" orthogonal step-growth mechanism where one thiol of the clickable dECM, DTT, or CGRGDS, reacted with one αMA, leading to a homogeneous distribution in crosslinks. The hybrid-hydrogel was then dynamically stiffened by sequentially reacting the residual αMA moieties in the presence of LAP photoinitiator via a light-initiated homopolymerization (FIG. 2A). Rheological measurements were performed to quantify the shear elastic modulus (G') of hybrid-hydrogels containing various amounts of clickable dECM and converted to elastic modulus (E') using rubber elasticity theory assuming a Poisson's ratio of 0.5. The elastic modulus scaled directly with total weight percent of clickable dECM as expected (FIG. 2B). The final formulation for the hybrid hydrogels consisted of 15 wt % PEGαMA and a molar thiol ratio of 75% DTT to 25% clickable dECM with 1 mM CCRGDS, and the soft hybrid-hydrogels exhibited an elastic modulus of 3.63±0.24 kPa within the range of healthy lung tissue (1 to 5 kPa) (FIG. 2C). Following sequential crosslinking, stiff hybrid-hydrogels were dynamically stiffened to an elastic modulus of 13.35±0.83 kPa replicating fibrotic stiffness (>10 kPa) and demonstrating temporal user control over in situ stiffening (FIG. 2C). The storage modulus and the equilibrium volumetric swelling ratio of hydrogels is proportional to the density of crosslinks within the polymer network and the equilibrium volumetric swelling ratio of the soft hybrid-hydrogels was approximately twice that of the stiffened hybrid-hydrogels indicating that crosslinking density increased following the stiffening reaction (FIG. 10).

Figures 2D, 2E:
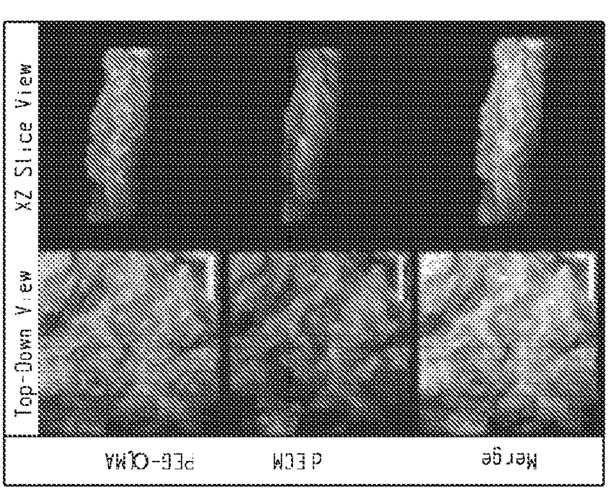
FIG. 2D depicts scanning electron micrographs of soft and stiffened hybrid hydrogels and shows an increase in interconnectedness in the stiffened hybrid hydrogels. Scale bar=25 μm.
FIG. 2E depicts representative confocal images of hybrid hydrogels stained for PEGαMA (green) and dECM (red) showing uniform mixing of the two components throughout the samples. Scale bar=50 μm.

Likewise, scanning electron micrographs showed a loosely organized morphology within the soft hybrid-hydrogels that became more highly interconnected upon stiffening (FIG. 2D). The initial thiol-Michael addition polymerization proceeded by a step-growth mechanism where one thiol reacted with one αMA. This mechanism produced a homogeneous distribution of PEGαMA and clickable dECM throughout hybrid-hydrogels as visualized by confocal microscopy (FIG. 2E).

Hydrolytic Stability

Figure 3A:
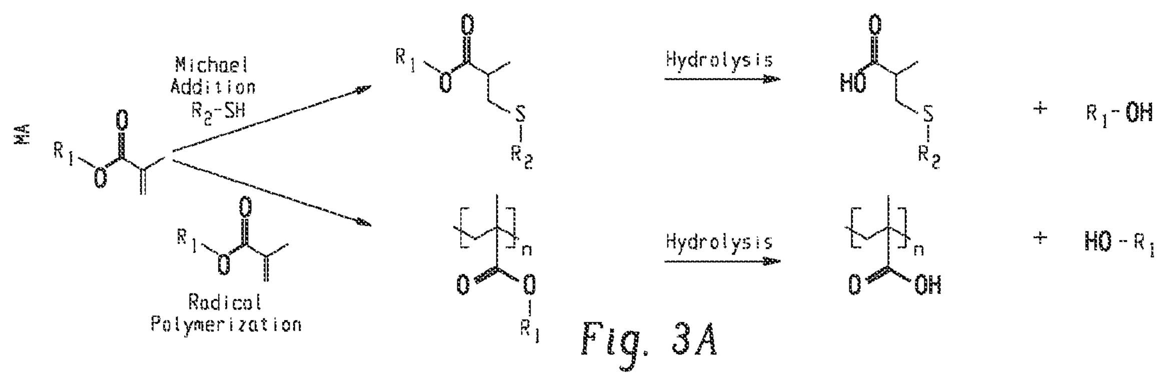
FIG. 3A depicts hydrolysis in traditional Michael-addition, thiol-ene biomaterials that occurs preferentially at ester linkages between PEG and the methacrylate (MA) functional end groups that leads to the breakdown of the polymer network.
Figure 3B:
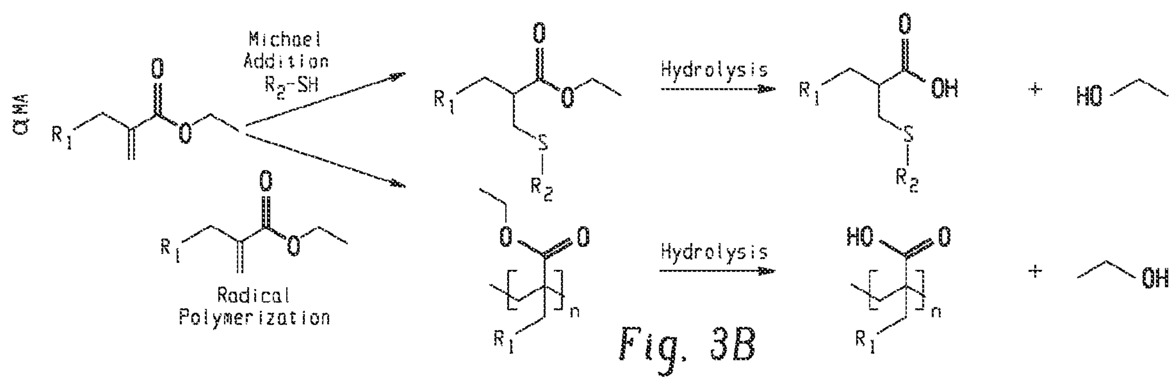
FIG. 3B depicts the hybrid-hydrogel system was designed to withstand hydrolysis by conjugating the MA to the PEG backbone on the opposite side of the carbonyl as a typical MA group, allowing hydrolysis to occur without affecting the crosslinked polymer network.
Figure 3C:
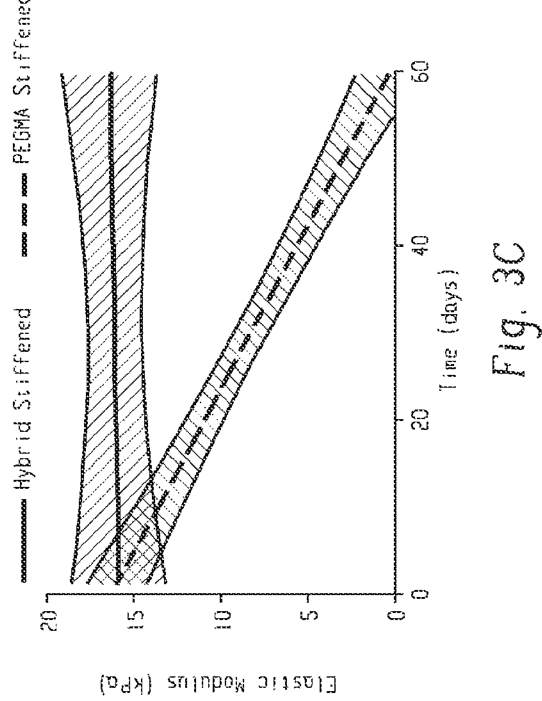
FIG. 3C depicts linear regression analysis of the elastic modulus for stiffened PEGαMA hybrid-hydrogels and PEGMA synthetic hydrogels showing that the elastic modulus of the hybrid-hydrogel did not significantly decrease over 60 days (m=0.009, p=0.81), while the elastic modulus of the PEGMA hydrogels significantly decreased (m=−0.265, $p<0.0001$). PEGMA hydrogel modulus values fell below the range considered pathological (>10 kPa) by Day 20 (n=4, shaded areas represent 95% confidence intervals).
Figure 3D:
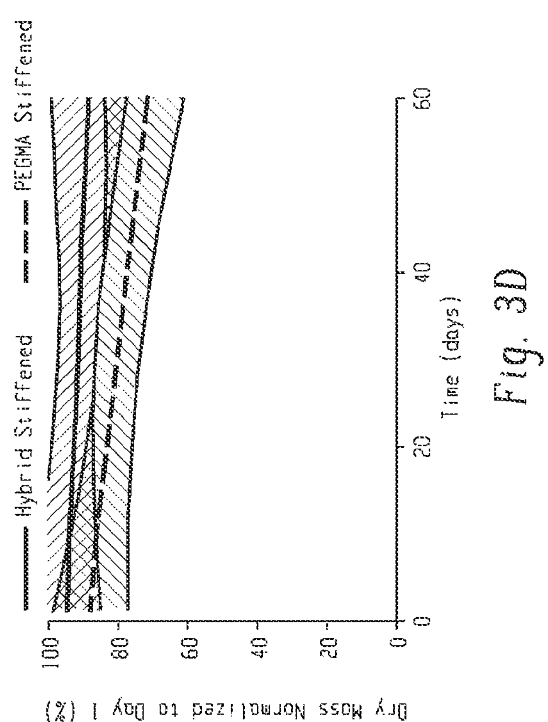
FIG. 3D depicts linear regression analysis of stiffened PEGαMA hybrid and PEGMA synthetic hydrogels dry mass measurements over 60 days and reveals that the PEGMA hydrogels may be losing mass at a faster rate than the hybrid-hydrogels (m=−0.576, p=0.086 versus m=−0.399, p=0.421, respectively), however these trends are not statistically significant.

Synthetic PEG-based hydrogels have been widely employed to study the cell-matrix interactions associated with the initiation of fibrotic disease. In vitro studies of fibroblast activation in response to modulus changes in PEG-based biomaterials have revealed that this differentiation is reversible when high modulus hydrogels (>15 kPa) are softened (<7 kPa). Hydrolysis in traditional Michael-addition, thiol-ene biomaterials occurs preferentially at ester linkages between the polymer backbone (e.g., PEG) and the acrylate or methacrylate (MA) functional end groups that facilitate polymerization, and this leads to the breakdown of the crosslinking points between the thiol-ene network and the network from the homopolymerization of the acrylate or MA groups (FIG. 3A). The presence of an ester bond between the PEG macromers and functional groups in many of these materials has resulted in irreversible hydrolytic degradation that degraded hydrogel samples completely within 21 days. The hybrid-hydrogel system in this article was designed to withstand hydrolysis over the long culture periods required to emulate chronic disease by conjugating the MA to the PEG chain on the opposite side of the carbonyl as a typical MA group. The placement of the ester in this unique functional group allows hydrolysis to occur without affecting the crosslinked polymer network, and a small alcohol is released (FIG. 3B). Additionally, the presence of the carbonyl group imparts high reactivity during chain-growth homopolymerization that is lacking for typical vinyl monomers. Hydrolytic stability of stiffened PEGαMA hybrid-hydrogels was monitored by measuring bulk mechanical properties and mass loss over 60 days in culture. These results were compared to stiffened, fully synthetic PEGMA. The elastic modulus of stiffened PEGαMA hybrid-hydrogels remained stable over 60 days, with a slope that was not significantly different from zero ($m=0.009$, $p<0.05$, linear regression) (FIG. 3C). The stiffened PEGMA hydrogel, however, began to degrade after just 10 days in PBS. The elastic modulus of this material decreased below a level recapitulating pathologic values between Day 10 and 20. Linear regression revealed that the PEGMA elastic modulus decreased significantly over time ($m=-0.265$, $p<0.0001$) (FIG. 3C). PEGMA hydrogels mass also decreased at a faster rate ($m=-0.576$, $p=0.086$, linear regression) than the stiffened PEGαMA hybrid-hydrogels ($m=-0.399$, $p=0.421$, linear regression), although these trends are not statistically significant (FIG. 3D).

Cell Viability

Figure 4A:
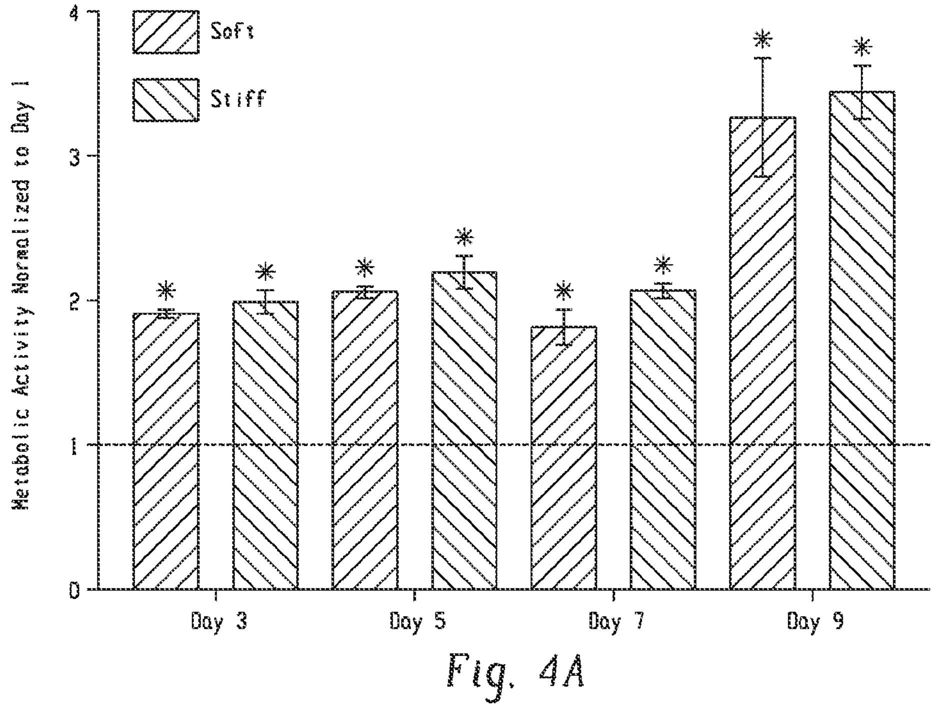
FIG. 4A depicts metabolic activity results from Days 3, 5, 7, and 9 that were normalized to initial readings at Day 1 and indicated that both soft and stiff hybrid-hydrogel substrates supported significantly increased levels of cellular viability through day 9. (n=6, mean±SEM, *: $p<0.05$, ANOVA, Tukey Test).
Figure 4B:
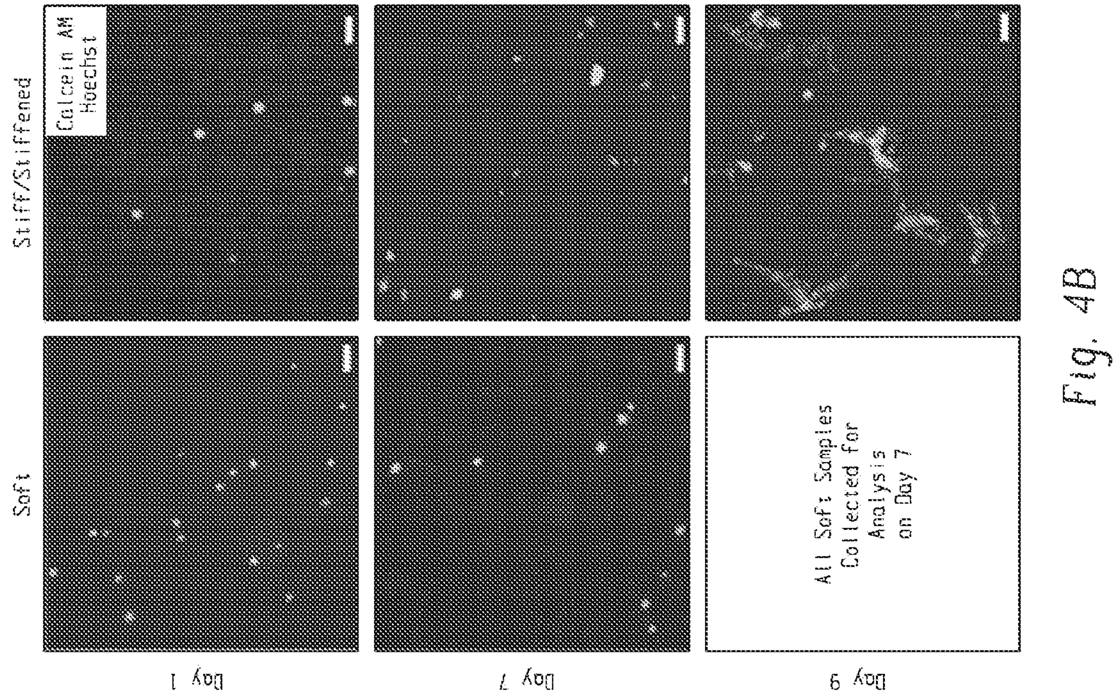
FIG. 4B depicts representative images of cells stained for Calcein-AM (green) and Hoechst (blue). Cells positive for green and blue are considered live, while cells stained for blue only are considered dead. Cells cultured on soft and stiff hydrogel substrates were analyzed on days 1 and 7. Cells cultured on soft hydrogels that were stiffened on day 7 were analyzed on day 9. Scale bar=25 μm.

To confirm that this new hybrid-hydrogel system was cytocompatible wildtype PDGFRα+ fibroblasts were seeded onto soft or stiff samples and metabolic activity was measured over time using a resazurin-based PrestoBlue™ Cell Viability assay. Metabolic activity significantly increased over nine days on both soft and stiff hybrid-hydrogels compared to day 1 (FIG. 4A). This increase in metabolic activity can be attributed to cellular proliferation over time. Representative images of cells stained for Calcein-AM (green) and Hoechst (blue) confirmed fibroblast viability on soft and stiff hybrid-hydrogels on days 1 and 7. All cells cultured on soft hybrid-hydrogels were analyzed on day 7, and then remaining soft hybrid-hydrogels that were stiffened on day 7 and analyzed on day 9 confirmed fibroblast viability through the dynamic stiffening process. Cells positive for green and blue were considered live, while cells stained for blue only were considered dead (FIG. 4B).

Cell Activation

It is well established that both composition and mechanical properties of ECM are significantly altered during the progression of fibrosis and that these alterations influence cellular function. Deciphering whether composition or mechanical properties are the major drivers of disease has remained challenging due to a limited number of experimental techniques which allow for precise spatiotemporal control over these parameters. Primary human lung fibroblasts have been cultured on acellular normal and fibrotic human lung slices that had significantly different moduli (1.6±0.08 kPa and 7.3±0.6 kPa, respectively) and a significant increase in the production of αSMA in the cells seeded on the fibrotic sections compared to cells on normal lung slices was observed. While the use of acellular normal and fibrotic human lung mimics the in vivo scenario, this system is not readily amenable for studying the relative contribution of ECM composition and stiffness. Recently, to overcome this limitation, polyacrylamide hydrogels of distinct moduli functionalized with solubilized dECM from control and fibrotic human lungs to decouple mechanical properties from substrate stiffness. This study found that substrate stiffness was the dominant factor initiating activation of fibroblasts, and pericytes cultured on medium (4.4±0.5 kPa) and high (23.7±2.3 kPa) modulus substrates that replicated transitioning and fibrotic human lung, respectively, expressed significantly increased levels of αSMA when compared to cells cultured on soft stiffness hydrogels (1.8 & 0.5 kPa) replicating healthy lung tissue. These results demonstrated that changes in αSMA expression and organization were mechanosensitive regardless of composition, however, this culture system does not allow for temporally changing mechanical properties over time. These systems enabled researchers to elucidate certain aspects regarding the influence of lung composition and stiffness on fibroblast activation in a static microenvironment; however, the remaining limitation was that these systems could not be altered over time, to recapitulate disease.

The hybrid-hydrogel system engineered and presented herein can dynamically recreate and decouple these aspects of disease initiation and progression in vitro. The ability of the hybrid-hydrogel system to provide temporal control over substrate modulus in the presence of cells permits the evaluation of the effect of dynamic modulus variation on primary murine PDGFRα+ dual-reporter fibroblasts. Here, PDGFRα+ dual-reporter fibroblasts were used to allow real-time analysis of fibroblast activation (i.e., col1a1 and (αSMA transgene expression). Briefly, PDGFRα+ dual-reporter fibroblasts were seeded onto soft hybrid-hydrogels, photoinitiator (LAP) was added to culture media on Day 6, and 365 nm UV light at 10 $mW/cm^2$ (hv) was applied for 5 minutes at Day 7 to stiffen these substrates. Fibroblast activation on these stiffened samples was compared to cells cultured on static soft and stiff hybrid-hydrogel controls (FIG. 5A). There was a significant increase in the expression of myofibroblast transgenes Col1a1 and αSMA, respectively, when PDGFRα+ dual-reporter fibroblasts were cultured on stiff (87.2%, 90.3%) and dynamically stiffened hydrogels (88.6%, 88.9%) compared to soft hydrogels (36.7%, 37.2%) (FIG. 5B, $p<0.0001$, ANOVA, Tukey Test). The higher level of expression of both transgenes on the stiffened hydrogels proved that the fibroblasts could be successfully activated in response to in situ stiffening. The higher levels of myofibroblast transgene expression on the stiffened hydrogels were comparable to those measured in cells cultured only on stiff hydrogels and demonstrates that the fibroblasts were activated in response to in situ stiffening. Representative images show a phenotypic transition from the PDGFRα+ dual-reporter fibroblasts cultured on the soft substrates from small and rounded to the cells elongating and forming distinct αSMA stress fibers on the stiff and stiffened substrates (FIG. 5C). This change in cellular morphology and the presence of αSMA stress fibers are a hallmark of the myofibroblast phenotype, and we attribute this change to the dynamic stiffening in the modulus.

Spatial heterogeneity is another hallmark of fibrotic disease that is important to replicate in vitro. Gradient stiffness polyacrylamide hydrogel substrates with modulus values ranging from 0.1 to 50 kPa that mimicked the increasing stiffness of crosslinked fibrotic lesions observed in murine bleomycin models showed notable transitions in fibroblast morphology to spindle-shaped cells typical of activated myofibroblasts observed in vivo at higher stiffness levels. Additionally, human lung fibroblasts seeded onto these materials expressed gradual increases in procollagen I and αSMA along the stiffness gradient, indicating that the matrix stiffness progressively activated fibroblasts. Another group investigated the influence of pattern size on hepatic stellate cells using UV-induced secondary crosslinking restricted with a photomask to spatially control mechanical properties with a modulus range of 2.5±0.6 kPa outside the patterns to 15.3±5.7 kPa within the patterns. There was an expression of high levels of αSMA and type I collagen on stiffer substrates, and the cells responded based on the local stiffness within the patterns, however, they remained quiescent on stiff substrates if the feature size was not sufficient to allow cell spreading.

Figures 6A, 6B, 6C:
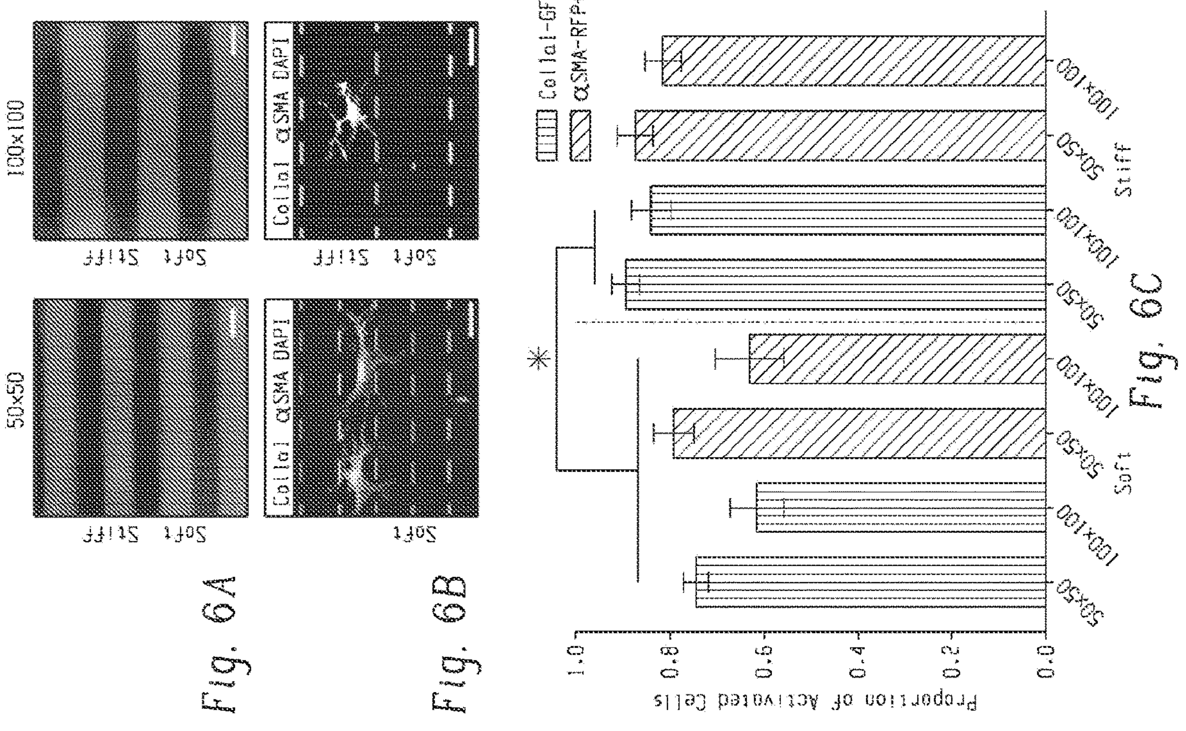
FIG. 6A depicts a chrome on quartz photomask with two line patterns of either 50- or 100-micron width and spacing was placed in close contact with the hybrid hydrogel surfaces, which were exposed to 365 nm, 10 mW/$cm^2$ at for 5 minutes, to spatially pattern defined regions of increased elastic modulus.
FIG. 6B depicts representative images of PDGFRα+ dual reporter cells on both patterns.
FIG. 6C depicts cells expressing significantly higher levels of col1a1 on both sizes within the stiff regions when compared to cells within the soft regions. There is an emerging trend of a bigger difference of expression with the larger spacing. This data is evidence of ability to spatially activate cells on the hybrid hydrogel system.

To investigate the influence of the spatial distribution of increases in matrix stiffness on PDGFRα+ dual-reporter fibroblasts over 7 days, patterned hybrid-hydrogels were fabricated by exposing soft substrates to light through a chrome-on-quartz photomask comprised of either 50- or 100-micron wide lines (FIG. 6A). Fibroblasts expressed significantly higher levels of the col1a1 transgene on both patterns within the stiff regions compared to the soft regions (FIG. 6B). Trends towards greater differences in expression were observed for both transgenes between the soft and stiff regions on the 100 micron pattern, demonstrating that tuning spatial patterning could impact the degree of cellular activation (FIG. 6C). Collectively, these studies have revealed that the phenotype of PDGFRα+ dual-reporter fibroblasts is highly dependent on substrate mechanical properties, and spatiotemporally stiffening can recreate the heterogeneous mechanical cues that cells encounter in vivo during fibrotic disease progression.

Synthesis of Ethyl-2-(Bromomethyl) Acrylate

The product was verified by proton nuclear magnetic resonance (NMR) performed on a Bruker Avance-III 300 NMR Spectrometer (7.05 T) for every reaction. The average functionalization was approximately 96% calculated by summing peak integration values and dividing by the 9 expected hydrogens. Product with functionalization greater than 90% was used in the synthesis of PEGαMA. A representative NMR spectrum can be seen in FIG. 7.

Synthesis of Poly(Ethylene Glycol)-Alpha Methacrylate

Product functionalization was verified by proton NMR. The degree of vinyl end group functionality was calculated using a ratio of the integration area of the proton resonance peak of $C{=}CH_2$ to that of the poly(ethylene glycol) (PEG) backbone. The representative NMR spectrum in FIG. 9 shows >98% functionality based on the integration ratio of peak C to the peak representing the PEG backbone.

Synthesis of Poly(Ethylene Glycol)-Methacrylate

The product functionalization was verified by proton NMR (FIG. 10). $^1$H NMR (300 MHz, $CDCl_3$): δ(ppm) 1.8 (t, 3H, $CH_3$—), 3.62 (s, 114H, PEG backbone), 4.17-4.21 (m, 2H, —$CH_2$—C(O)—O—O) 5.60 (t, 1H, —$C{=}CH_2$), 6.0 (d, 1H, —$C{=}CH_2$).

Equilibrium Swelling Ratio

The experimental equilibrium swelling ratio for the soft hybrid hydrogel reached 9.10±0.141 within 6 hours and the stiffened hybrid hydrogel reached 4.81±0.0914 within 6 hours (FIG. 10). The experimental swelling ratio for the soft hydrogel was approximately 2 times the experimental equilibrium swelling ratio of the stiffened hydrogel an indication that the secondary crosslinking reaction is in fact increasing overall crosslinking density after stiffening.

Here, a hydrolytically stable hybrid-hydrogel stiffening system with clickable dECM and a phototunable PEG backbone was synthesized and characterized. These hybrid-hydrogels integrated complex biologically relevant compositions into biomaterials that facilitated spatiotemporal control over mechanical properties to generate a platform for studying the dynamic molecular and cellular mechanisms underlying fibrosis. The dual-stage polymerization mechanism provided control over initial elastic modulus and supported spatiotemporal control over precise increases in local mechanical properties in situ, recreating the heterogeneous ECM stiffening that cells encounter in vivo. Using pulmonary fibrosis as a model of chronic fibrotic disease, this in in vitro system was used to investigate the response of PDGFRα+ fibroblasts from dual-transgenic reporter mice to local matrix stiffening. Experimental results indicated that fibroblasts cultured on stiff and temporally stiffened substrates with moduli replicating diseased tissue exhibited increased activation through the measurement of Coll a1 and αSMA transgene expression compared to those grown on soft substrates replicating healthy tissue (FIG. 5B,C). A phenotypic transition from quiescent to activated fibroblasts as demonstrated by the expression and organization of αSMA stress fibers was initiated by exploiting a sequential crosslinking reaction scheme in these novel hybrid-hydrogels. Presented herein, clickable dECM provided the complex compositional properties of healthy lung ECM, however, future experiments could include clickable dECM derived from fibrotic dECM to enable the decoupling of fibrotic tissue composition from mechanics for fundamental studies to probe how fibroblasts interact with and receive information from the extracellular microenvironment. This versatile system will also enable the encapsulation of healthy or fibrotic PDGFRα+ fibroblasts within 3D hybrid-hydrogels to investigate cellular responses to dynamic biophysical changes in the extracellular environment in a more physiologically relevant way. Harnessing independent and dynamic control over the presentation of biochemical and biophysical cues to cells cultured within 3D hybrid-hydrogels will enable the design of sophisticated experiments that will improve our ability to study the cellular and molecular mechanisms underlying fibrotic disease initiation and progression.

Example 2

Synthesize and Characterize Hydrogel Precursors:

Step 1

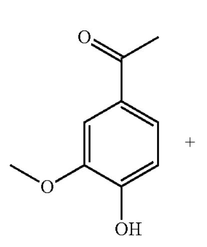

+

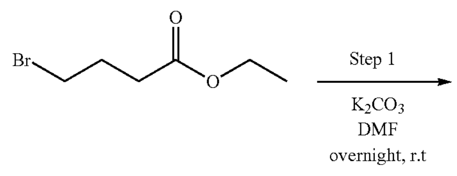

-continued

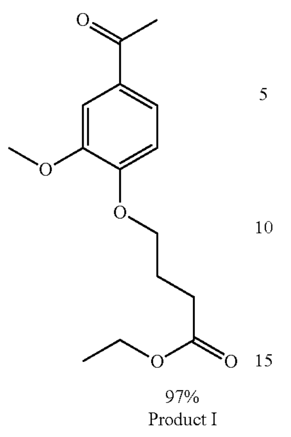

Product I

Acetovanillone (30 g, 180.5 mmol), DMF (150 ml), and ethyl 4-bromobutyrate (31 ml, 217 mmol) were added to an argon purged flame dried schlenk flask (500 ml). Then potassium carbonate (37.4 g, 271 mmol) was added to the mixture, which formed a suspension. The reaction mixture was stirred at room temperature overnight under argon, and the reaction mixture was poured into a 2000 ml beaker filled with DI water while stirring. Then it was cooled to 4° C. and kept overnight to get the maximum yield of the product. The product was vacuum filtered and freeze-dried to obtain off white/light yellow color solid product (Product I). (yield 97%). The Product I was characterized using NMR. $H^1$ NMR spectrum of Product I ($CDCl_3$, 300 MHz): δ (ppm) 1.30 (t, 3H), 2.24 (p, 2H), 2.58 (t, s, 5H), 3.93 (s, 3H), 4.19 (t, q, 4H), 6.92 (d, 1H), 7.57 (dd, 2H).

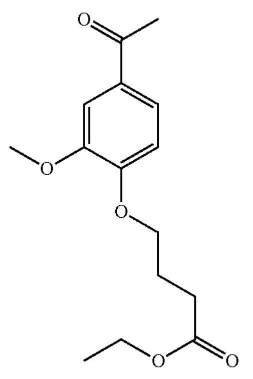
Product I

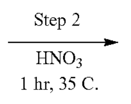

-continued

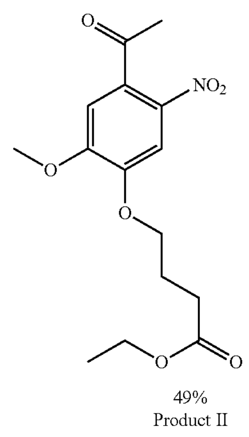

Product II

The Product I was split in half (2×~25) g and step 2 was carried out twice. For each portion of Product I, $HNO_3$ (70 ml) was used. To a single neck round bottom flask (1000 ml) with a magnetic stir bar, $HNO_3$ was added. It was cooled to 5° C. using an ice bath. The Product I was added in small portions to the $HNO_3$. After adding all the powder, the reaction mixture was heated to 35° C. using a water bath and then placed back on the ice bath until the reaction mixture was cooled to ~20° C. This process was repeated until the reaction mixture in the water bath is 1 hour. Bright red/brown color reaction mixture was poured into chilled DI water while stirring. To complete the precipitation, the reaction mixture was kept overnight at 4° C. The precipitate was filtered and recrystallized using absolute ethanol. The product was vacuum filtered and freeze-dried to obtain a yellow/orange color solid product (Product II). (yield 49%). Product II was characterized using NMR. $H^1$ NMR spectrum of Product I ($CDCl_3$, 300 MHz): δ (ppm) 1.41 (t, 3H), 2.34 (p, 2H), 2.63 (t, s, 5H), 4.01 (s, 3H), 4.25 (t, q, 4H), 6.84 (S, 1H), 7.67 (S, 1H).

Step 3

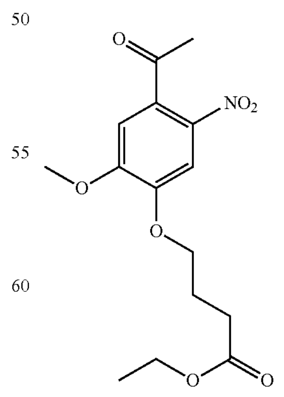
Product II

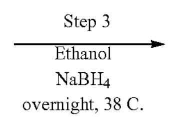

-continued

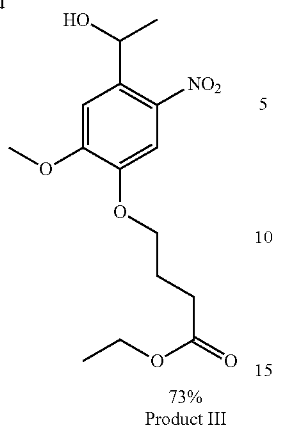

A flame-dried, argon purged schlenk flask was charged with absolute ethanol (500 ml). Product II (21.9 g, 67 mmol) and sodium borohydride (1.63 g, 43 mmol) were added and heated the reaction mixture 38° C. and stirred overnight. Bright red/orange color reaction mixture was poured into chilled DI water while stirring. To complete the precipitation, the reaction mixture was kept overnight at 4° C. The precipitate was vacuum filtered and freeze-dried to obtain a light yellow color solid product (Product III). (yield 73%). Product III was characterized using NMR. $H^1$ NMR spectrum of Product III ($CDCl_3$, 300 MHz): δ (ppm) 1.30 (t, 3H), 1.58 (d, s, 4H), 2.25 (p, 2H), 2.59 (t, 2H), 4.00 (s, 3H), 4.21 (t, q, 4H), 5.65 (q, 1H), 7.34 (s, 1H), 7.62 (s, 1H).

-continued

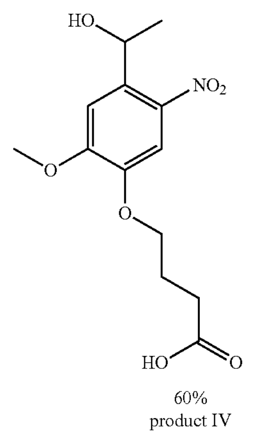

The Product III (16.12 g, 49 mmol) was mixed with trifluoro acid (TFA) (45 ml) and heated the reaction mixture to 87° C. stirred for 8 hours. After 8 hours, again, TFA (20 ml) was added and stirred overnight. Another portion of TFA (20 ml) was added to complete the reaction and stirred for 4 hours. After four hours, the reaction mixture was filtered, and it was kept overnight at 4° C. A brownish yellow color precipitate was formed. The precipitate was vacuum filtered and freeze-dried to obtain brown-yellow color solid product (Product IV). (yield 60%). Product IV was characterized using NMR. $H^1$ NMR spectrum of Product IV (DMSO, 300 MHz): δ (ppm) 1.40 (d, 3H), 2.01 (p, 2H), 2.44 (t, 2H), 2.09 (broad s, 2H), 3.93 (s, 3H), 4.09 (t, 2H), 5.33 (q, 1H), 7.41 (s, 1H), 7.58 (s, 1H).

Step 4

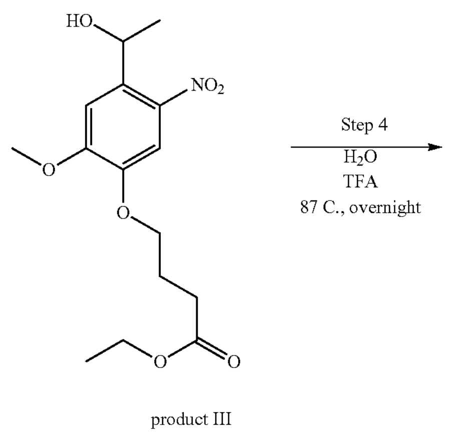

Step 5

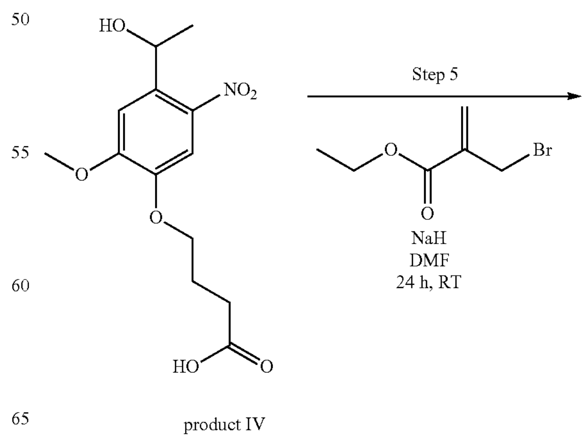

-continued

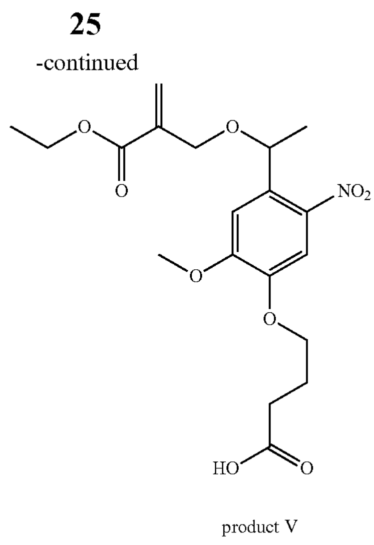

product V

A flame dried, argon purged schlenk flask was charged with DMF (150 ml). Product IV (4.5 g, 15 mmol was dissolved in DMF. Sodium hydride (0.51 g, 21 mmol) was added at 0° C. to the reaction mixture. Then, Ethyl 2-(bromomethyl) acrylate (4 ml, 28 mmol) was added to the reaction mixture. The reaction mixture was kept overnight at 4° C. To quench the reaction, 3 M HCl was added at 0° C. until the reaction mixture gets clear. The reaction mixture was extracted with ethyl acetate, followed by brine and DI water. The organic layer was concentrated, and obtained a yellow color oil was separated. Purification was done by column chromatography using a hexane: ethyl acetate (1:1) solvent mixture. A bright yellow color solid was isolated after the vacuum filtration (Product V). (yield 78%). Product IV was characterized using $^1$H and $^{13}$C NMR. H$^1$ NMR spectrum of Product V ($CDCl_3$, 300 MHz): δ (ppm) 1.30 (t, 3H), 1.54 (d, 3H), 2.23 (p, 2H), 2.62 (t, 2H), 2.72 (broad s, H), 3.98 (s, 3H), 4.13 (t, 2H), 4.25 (q, 2H), 4.84 (s, 2H), 5.57 (q, 1H), 5.83 (s, 1H), 6.35 (s, 1H), 7.28 (s, 1H), 7.53 (s, 1H).

Figure 11:
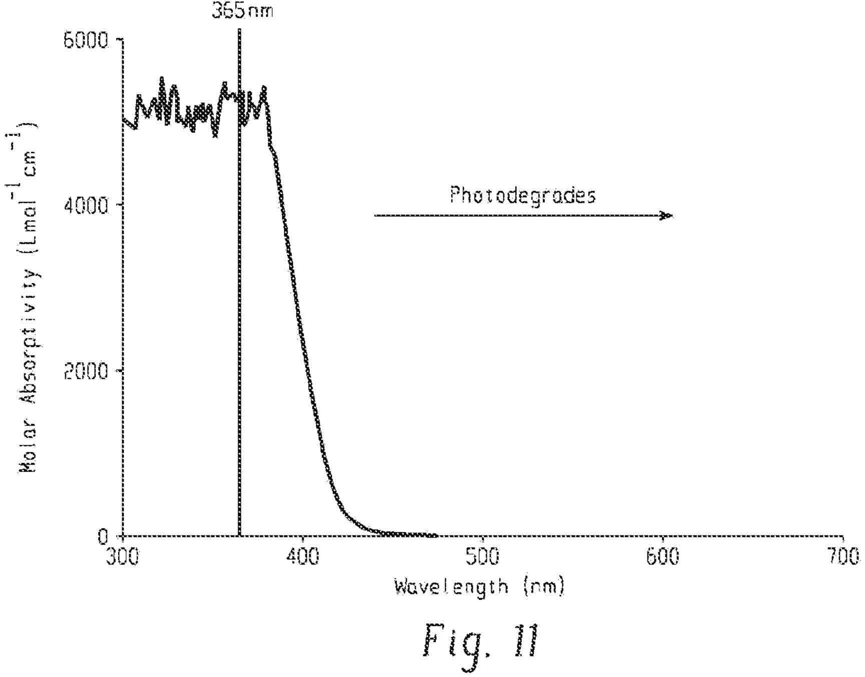
FIG. 11 depicts a plot of Molar absorptivity vs. wavelength for Product V, a hydrogel precursor of Example 2.
Figure 12:
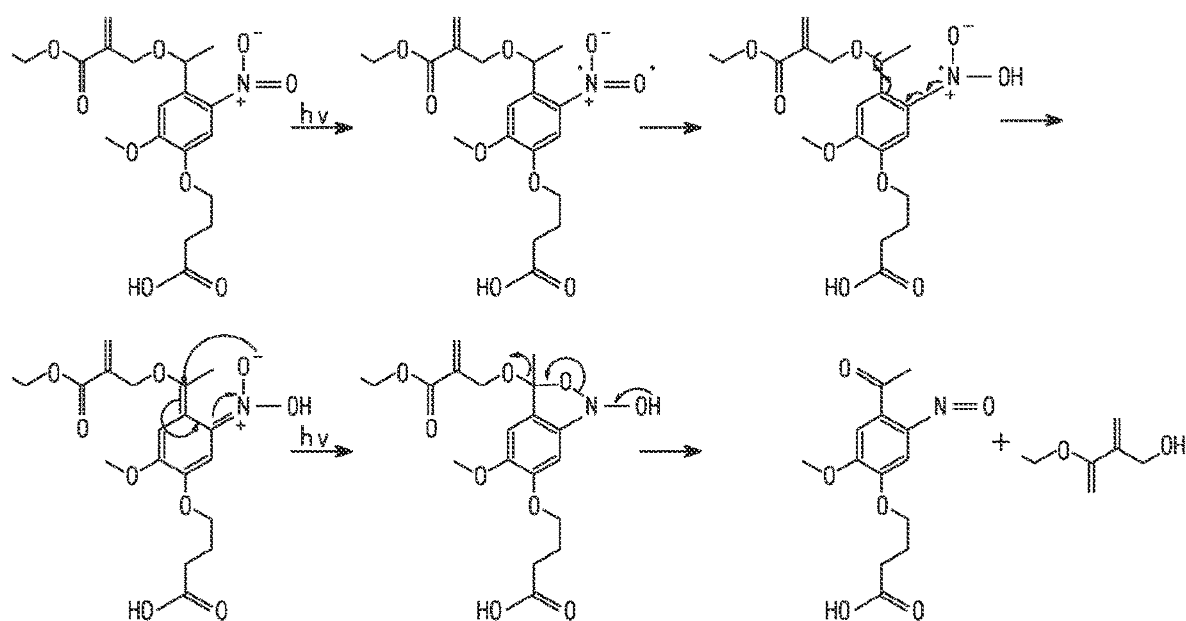
FIG. 12 depicts a proposed mechanism for the cleavage of the nitrobenzyl ether moiety of Product V with light.

Photo-Degradability of Product V:

The molar absorptivity of the Product V was calculated by measuring the absorbance of a Product V solution in water: DMSO (80:20 v/v) blend at the concentrations of 0.004 mM. The absorbance was measured on a UV-visible spectrophotometer (NanoDrop Spectrophotometer ND-1000), and the molar absorptivity was calculated from the absorbance. (FIG. 11). Product V absorbs light strongly in the UV (peak at 365 nm) with a tail that extends into the visible (>405 nm) and may undergo an irreversible cleavage upon absorption of light at higher wavelengths (See FIG. 12, mechanism for the cleavage of the nitrobenzyl ether moiety of product V with light).

Example 3: Thiolation of dECM

Thiolation of Healthy Mouse Lungs

Quantification of $NH_2$ in dECM

Figure 13:
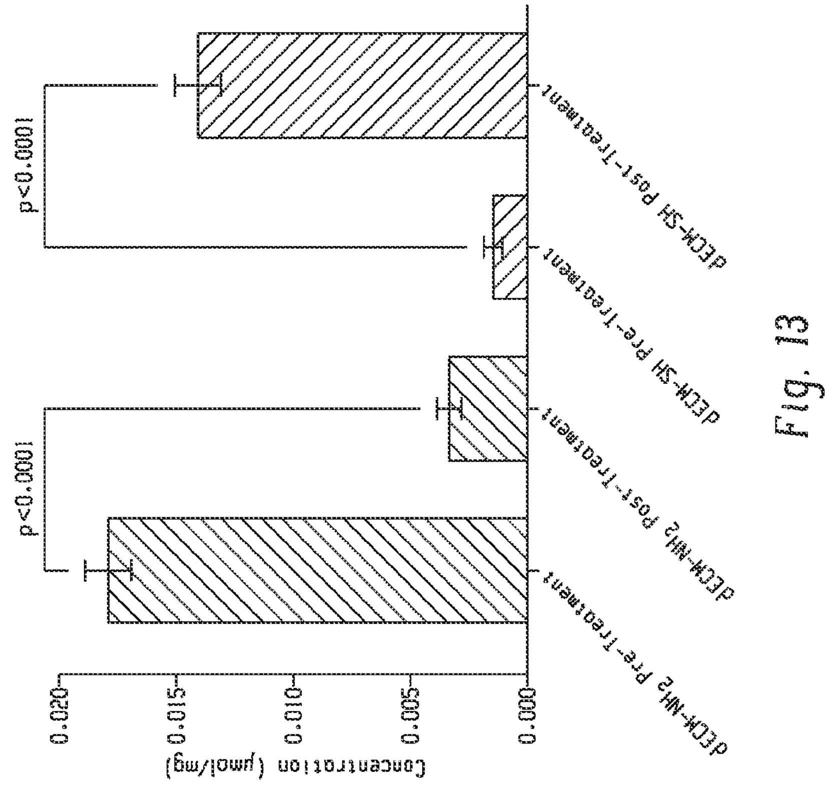
FIG. 13 depicts variation of amine and thiol concentration of mouse lung dECM pre- and post-treatment with Traut's reagent; (n=7, p<0.0001, ANOVA).

The primary amine content in dECM was quantified using a ninhydrin (NHN; Sigma) assay according to the manufacturer's protocol with cysteine as the standard. This was performed before thiolation and after thiolation. (See, FIG. 13).

Optimization of Traut's Reagent (2-Iminothiolane Hydrochloride) Molar Excess for Thiolation

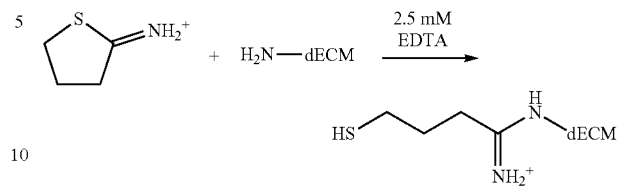

Figure 14:
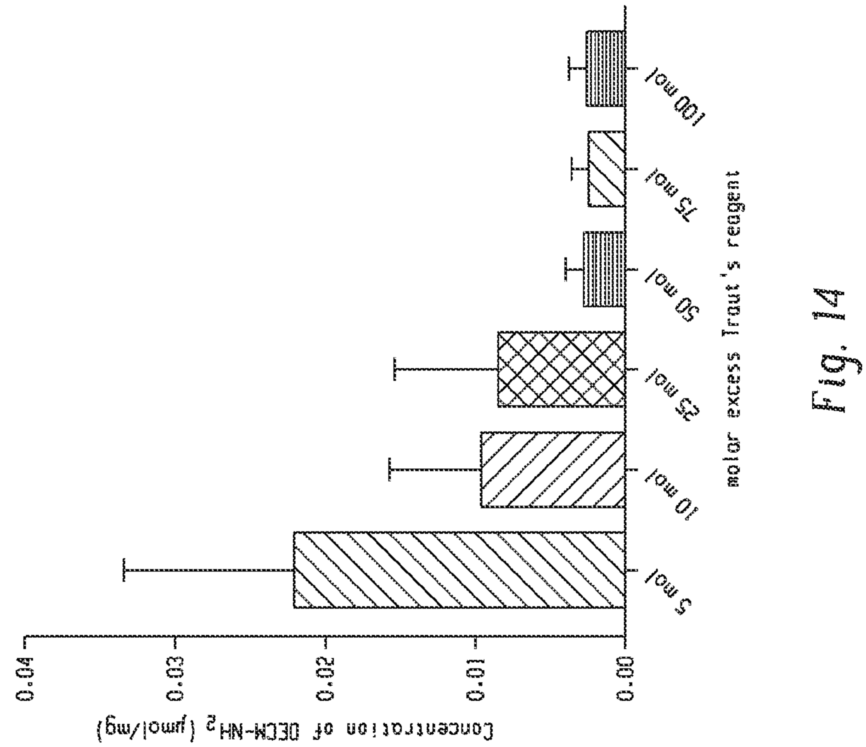
FIG. 14 depicts thiolation of mouse lung dECM with various Traut's reagent molar excess; (n=4, t-test).

Traut's reagent at 3 mg/mi solution in PBS with 2.5 mM ethylenediaminetetraacetic acid (EDTA; Thermofisher) solution was used, dECM was dissolved in various amounts of Traut's solution in order to obtain 5, 10, 25, 50, 75, and 100 molar excess. Samples were incubated for 2 hours at mom temperature. Thiolated dECM was extracted using desalting columns. (See, FIG. 14).

Thiolation of Mouse Lungs

According to FIG. 5, Traut's reagent 50 molar excess was the optimized molar excess for thiolation. Hence, the dECM was reacted with a 50-molar excess Traut's reagent to primary amine concentration with 2.5 mM EDTA for 2 h at room temperature. Thiolated dECM was extracted using desalting columns, and the final solution was lyophilized to get a dry powder of thiolated dECM.

Quantification of SH in dECM

The thiol content was quantified using Ellman's reagent (5,5-dithio-bis-(2-nitrobenzoic acid) or DTNB; Sigma) according to the manufacturer's protocol using glycine as the standard. This was performed before thiolation and after thiolation. (See, FIG. 13).

Thiolation of Human dECM

Optimization of thiolation of human dECM was carried out using the same protocol as mouse lung dECM. (See FIG. 15).

Figure 15:
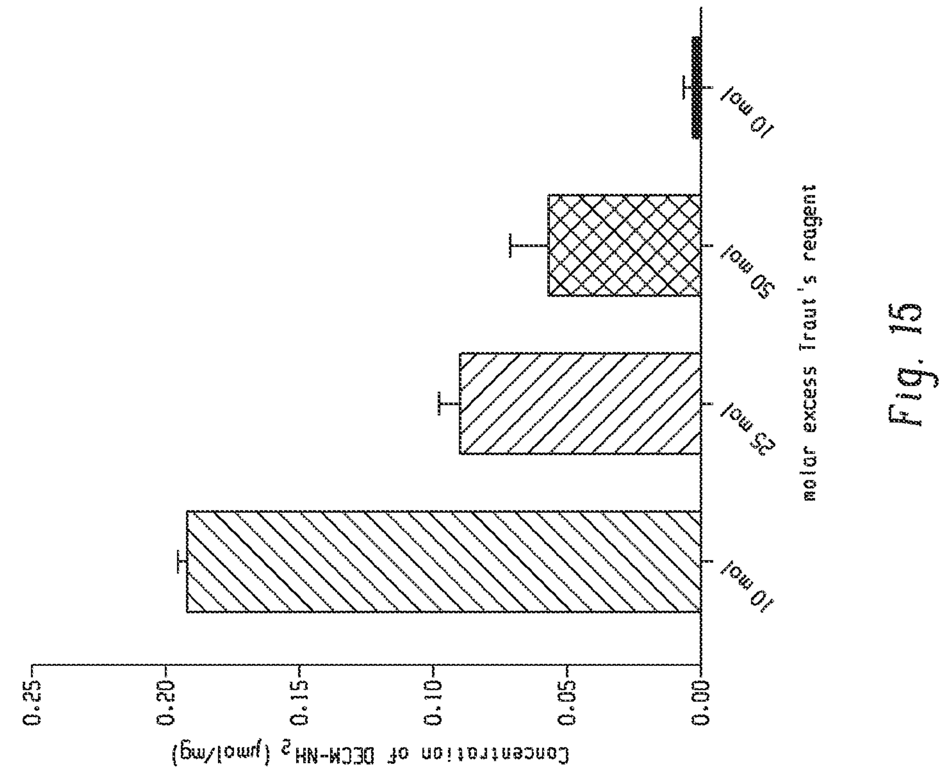
FIG. 15 depicts thiolation of human dECM with various Traut's reagent molar excess; (n=3, t-test).

According to FIG. 15. Traut's reagent 75 molar excess was the optimized molar excess for thiolation. Hence, the dECM was reacted with a 75-molar excess Traut's reagent to primary amine concentration with 2.5 mM EDTA for 2 h at room temperature.

Figure 16:
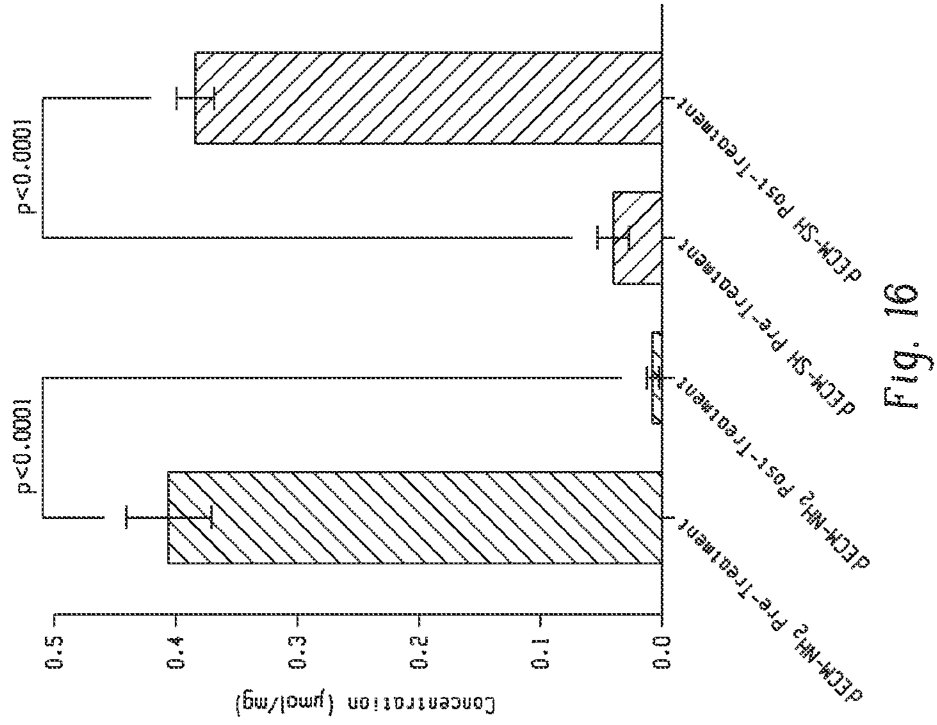
FIG. 16 depicts variation of amine and thiol concentration of human dECM pre- and post-treatment with Traut's reagent; (n=3, p<0.0001, ANOVA).

The thiol content was quantified using Ellman's reagent (5,5-dithio-bis-(2-nitrobenzoic acid) or DTNB; Sigma) according to the manufacturer's protocol using cysteine as the standard. This was performed before thiolation and after thiolation. The primary amine content in dECM was quantified using a ninhydrin (NHN; Sigma) assay according to the manufacturer's protocol with glycine as the standard. This was performed before thiolation and after thiolation. (See, FIG. 16).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A hybrid hydrogel scaffold comprising:

a decellularized extracellular matrix (dECM) tissue comprising lung tissue, and a synthetic polymer crosslinked with the dECM, wherein the dECM is thiolated and wherein the synthetic polymer comprises alpha-methacrylate functionality and has a photo-tunable stiffness; and a molar excess of alpha-methacrylate functionality of the synthetic polymer to the thiol of the dECM.

2. The hybrid hydrogel of claim 1, wherein the synthetic polymer comprises poly(ethylene glycol)-alpha-methacrylate or poly(ethylene glycol) linked to an alpha-methacrylate through a degradable linker group.

3. The hybrid hydrogel of claim 1, wherein the synthetic polymer is photo-tuned to having a patterned stiffness greater than about 0.5 kPa.

4. The hybrid hydrogel of claim 1, wherein the dECM tissue comprises mammalian tissue.

5. The hybrid hydrogel of claim 1, wherein a degradable linker group covalently links the synthetic polymer to the alpha-methacrylate functionality and the degradable linker group is an enzyme-degradable, a protease-degradable, photodegradable, and/or a biodegradable group.

6. The hybrid hydrogel of claim 5, wherein the degradable group is a matrix metalloprotease (MMP) degradable group; a photodegradable group degraded through exposure to visible light (380 nm-760 nm) photoexcitation; or a photodegradable group degraded through exposure to ultraviolet (UV) light photoexcitation (100 nm-380 nm).

7. The hybrid hydrogel of claim 5, wherein the degradable linker group is a photodegradable group.

8. A hybrid hydrogel system comprising:

the hybrid hydrogel scaffold of claim 1 and a plurality of cells.

9. The hybrid hydrogel system of claim 8, wherein the synthetic polymer is photo-tunable to a stiffness in the rage of from about 0.5 kPa to at least about 10 kPa.

10. The hybrid hydrogel system of claim 9, wherein the synthetic polymer is photo-tunable using UV light.

11. The hybrid hydrogel system of claim 8, wherein the plurality of cells comprises fibroblasts.

12. A method for generating a hybrid hydrogel, the method comprising:

preparing a thiolated dECM, preparing a synthetic polymer solution, chemically crosslinking the dECM and the synthetic polymer, swelling the crosslinked dECM and synthetic polymer using one or more swelling solutions, thereby generating a hydrogel, selectively photo-crosslinking the swelled hydrogel using a patterned mask, seeding a plurality of cells onto the photo-crosslinked hydrogel, and culturing the cells on the pattern-photo-crosslinked hydrogel.

13. The method of claim 12, wherein the synthetic polymer comprises one or more of poly(ethylene glycol), functionalized poly(ethylene glycol), poly(ethylene oxide), poly (vinyl alcohol), poly(vinyl acetate), poly(ethylene imine), polyacrylamide, poly(hydroxylethyl methacrylate), poly(N-vinyl pyrrolidone), poly(methacrylic acid), poly(butyl methacrylate), poly(methyl methacrylate), poly(meth acrylic acid), poly(N-isopropyl acrylamide), poly(hydroxylethyl-methacrylate), acrylate-functionalized gelatin, methacrylate-functionalized poly(ethylene glycol), methacrylate-functionalized gelatin, acrylate-functionalized hyaluronic acid, and methacrylate-functionalized hyaluronic acid.

14. The method of claim 12, wherein the synthetic polymer is functionalized with at least one functional moiety that is acrylate, methacrylate, alpha-methacrylate, norbornene, thiol, azide, alkene, alkyne, oxime, hydrozone, isocyanate, tetrazine, maleimide, vinyl sulphone, dibenzocyclooctyne, or NHS-ester.

15. The method of claim 12, wherein a degradable linker group covalently links the synthetic polymer to the at least one functional moiety.

16. The method of claim 15, wherein the degradable linker group is enzyme-degradable, protease-degradable, photodegradable, and/or biodegradable groups.

17. The method of claim 16, wherein the degradable group is a matrix metalloprotease (MMP) degradable group; a photodegradable group degraded through exposure to visible light (380 nm-760 nm) photoexcitation; or a photodegradable group degraded through exposure to ultraviolet (UV) light photoexcitation (100 nm-380 nm).

18. The method of claim 15, wherein the degradable linker group is an ortho-nitrobenzyl moiety, coumarin, azobenzene, rotaxane, aromatic disulfides, poly(glycerol sebacate) (PGS), polylactic-glycolic acid (PLGA), polylactic acid (PLA), poly-caprolactone (PCL), copolymers of polylactic-glycolic acid and poly-caprolactone (PCL-PLGA copolymer), copolymers of polyethylene glycol and polycaprolactone (PEG-PCL copolymer), copolymers of polyethylene glycol and trimethylene carbonate (PEG-TMC copolymer), copolymers of polyethylene glycol and poly (glycerol sebacate) (PEG-PGS copolymer), copolymers of polylactic-glycolic acid and poly-lactic acid (PLGA-PLA copolymer), polyhydroxy-butyrate-valerate (PHBV), polyorthoester (POE), polyethylene oxide-butylene terephthalate (PEO-PBTP), poly-D,L-lactic acid-p-dioxanone-polyethylene glycol block copolymer (PLA-DX-PEG), spermine, 2,2'-(ethylenedioxy)bis(ethylamine) (EDBE), CGPQGIWGQGC peptide, GPQGIAGQ peptide (PCL-1), or IPVSLRSG peptide (PCL-2).

19. The method of claim 12, wherein the synthetic polymer comprises poly(ethylene glycol)-alpha-methacrylate or poly(ethylene glycol) linked to an alpha-methacrylate through a degradable linker group.

20. A method of evaluating fibrosis in a population of cells, the method comprising:

seeding a plurality of cells onto the hybrid hydrogel of claim 1, culturing the cells for a duration of time, and evaluating the expression of fibrotic phenotypic markers in the cultured cells.

* * * * *